(12) United States Patent
Brown et al.

(10) Patent No.: US 6,207,422 B1
(45) Date of Patent: Mar. 27, 2001

(54) PROTEIN THAT ENHANCES EXPRESSION OF POTASSIUM CHANNELS ON CELL SURFACES AND NUCLEIC ACIDS THAT ENCODE THE SAME

(75) Inventors: Arthur M. Brown, Brecksville; Barbara A. Wible, Cleveland; Qing Yang, S. Euclid, all of OH (US)

(73) Assignee: The MetroHealth System, Cleveland, OH (US)

( * ) Notice: Subject to any disclaimer, the term of this patent is extended or adjusted under 35 U.S.C. 154(b) by 0 days.

(21) Appl. No.: 09/062,440

(22) Filed: Apr. 17, 1998

(51) Int. Cl.$^7$ ............... C12P 19/34; C12Q 1/68; C07H 21/02; C07H 21/04
(52) U.S. Cl. ............ 435/91.1; 435/6; 435/91.2; 435/69.1; 536/23.1; 536/23.4; 536/23.5; 536/24.3; 536/24.31; 536/24.33
(58) Field of Search ............... 435/6, 91.1, 91.2, 435/69.1; 536/23.1, 23.4, 23.5, 24.3, 24.31, 24.33

(56) References Cited

U.S. PATENT DOCUMENTS

| | | |
|---|---|---|
| 5,492,825 | 2/1996 | Jan et al. . |
| 5,670,335 | 9/1997 | Jan et al. . |
| 5,756,669 | * 5/1998 | Bishcoff et al. ............ 530/350 |
| 5,856,449 | 1/1999 | Groppi, Jr. et al. . |
| 5,882,873 | 3/1999 | Bienkowski et al. . |

FOREIGN PATENT DOCUMENTS

WO9531544 * 11/1995 (WO) .

OTHER PUBLICATIONS

"Cloning and Characterization of Gu/RH–II Binding Protein" by Valdez, et al., *Biochemical and Biophysical Research Communications*, 234, 1997, pp. 335–340.

"Specific Inhibition of Stat3 Signal Transduction by PIAS3" by Chung, et al., *Science*, vol. 278, Dec., 1997, pp. 1803–1805.

"Mizl, a novel zinc finger transcription factor that interacts with Msx2 and enhances its affinity for DNA" by Wu, et al., *Mechanisms of Development* 65, 1997, pp. 3–17.

"Cloning and Expression of a Novel K+ Channel Regulatory Protein, KChAP", Wible, et al., *Journal of Biological Chemistry*, vol. 273, No. 19, May 8, 1998, pp. 11745–11751.

* cited by examiner

Primary Examiner—Kenneth R. Horlick
Assistant Examiner—Jeffrey Siew
(74) Attorney, Agent, or Firm—Calfee, Halter & Griswold LLP

(57) ABSTRACT

The present invention provides polynucleotides that encode a protein, designated herein as K+ Channel Associated Protein or "KChAP". It has been determined that expressing polynucleotides that encode KChAP in host cells, along with polynucleotides that encode the Kvα channel subunit Kv 2.1, the Kvα channel subunit Kv 2.2, the Kvα channel subunit Kv 1.3, or the Kvα channel subunit Kv 4.3, increases the number of Kv2.1, Kv 2.2, Kv1.3 or Kv4.3 channels, respectively, in the plasma membrane of such cells. The present invention also relates to a method of making cells that have increased numbers of Kv channels on the plasma membranes thereof and to a method of using such cells as model systems for studying the effect of pharmacological agents on Kv channels, particularly on Kv2.1, Kv 2.2, Kv 1.3, and Kv 4.3 channels. The present invention also relates to the protein KChAP.

13 Claims, 11 Drawing Sheets

Figure 2

```
    atgaagatcaaagaactttaccgcaggcgctttccccggaagaccctggggccttccgat
1   ---------+---------+---------+---------+---------+---------+ 60
    M  K  I  K  E  L  Y  R  R  R  F  P  R  K  T  L  G  P  S  D  - ctctctttgctctctttgcccctggcacctctcctgtaggctcccccagccccttgct
61  ---------+---------+---------+---------+---------+---------+ 120
    L  S  L  L  S  L  P  P  G  T  S  P  V  G  S  P  S  P  L  A  -
                                            A
                                            p
                                            a
                                            I
    tccattcctcccaccctcctgacccctggcaccttgctgggccctaagcgtgaggtggac
121 ---------+---------+---------+---------+---------+---------+ 180
    S  I  P  P  T  L  L  T  P  G  T  L  L  G  P  K  R  E  V  D  -
                               A
                               a
                               t
                               I
                               I
    atgcaccctcctctgccccagcctgtgcaccctgacgtcaccatgaaaccactgcccttc
181 ---------+---------+---------+---------+---------+---------+ 240
    M  H  P  P  L  P  Q  P  V  H  P  D  V  T  M  K  P  L  P  F  -
                      E
                      a
                      g
                      I
    tacgaagtctacggagagctcatccggccgaccacccttgcgtccacctccagtcagagg
241 ---------+---------+---------+---------+---------+---------+ 300
    Y  E  V  Y  G  E  L  I  R  P  T  T  L  A  S  T  S  S  Q  R  -
                                     P
                                     v      p
                                     u      s
                                     I      t
                                     I      I
    tttgaggaagcccactttacctttgcactcactccccagcagctgcagcagattctcaca
301 ---------+---------+---------+---------+---------+---------+ 360
    F  E  E  A  H  F  T  F  A  L  T  P  Q  Q  L  Q  Q  I  L  T  -
```

Figure 2 (continued)

```
     tccagggaggttctgccaggagccaagtgcgattataccatacaagtgcagctcaggttc
361  ---------+---------+---------+---------+---------+---------+  420
     S  R  E  V  L  P  G  A  K  C  D  Y  T  I  Q  V  Q  L  R  F   -
                            P
                            v
                            u
                            I
                            I
     tgtctctgtgagaccagctgcccccaggaggactatttccccctaacctctttgtcaag
421  ---------+---------+---------+---------+---------+---------+  480
     C  L  C  E  T  S  C  P  Q  E  D  Y  F  P  P  N  L  F  V  K   -
                                  B
                                  s
                                  t
                                  E
                                  I
                                  I
     gttaatgggaaactctgccccctgccgggttacctccctccaaccaagaatggagctgag
481  ---------+---------+---------+---------+---------+---------+  540
     V  N  G  K  L  C  P  L  P  G  Y  L  P  P  T  K  N  G  A  E   -
              S
              t
              u
              I
     cccaagaggcctagtcgtccaatcaacatcacaccctggctcgtctctcagccactgtt
541  ---------+---------+---------+---------+---------+---------+  600
     P  K  R  P  S  R  P  I  N  I  T  P  L  A  R  L  S  A  T  V   -
                                  H
                                  p
                                  a
                                  I
     cccaacaccatagtggttaactggtcatctgagtttggacggaattactccttgtctgtg
601  ---------+---------+---------+---------+---------+---------+  660
     P  N  T  I  V  V  N  W  S  S  E  F  G  R  N  Y  S  L  S  V   -
                                                                B
                             P                                  s
                             s                                  a
                             t                                  W
                             I                                  I
     tacctggtgaggcagttgactgcagggaccctgctacaaaagctcagagccaagggtatc
661  ---------+---------+---------+---------+---------+---------+  720
     Y  L  V  R  Q  L  T  A  G  T  L  L  Q  K  L  R  A  K  G  I   -
                 A
                 v
                 a
```

Figure 2 (continued)

```
                  I
      cggaatccagaccattcccgagcactgatcaaggagaaattgactgctgaccccgacagt
721   ---------+---------+---------+---------+---------+---------+   780
       R  N  P  D  H  S  R  A  L  I  K  E  K  L  T  A  D  P  D  S    - gaagtggctactacaagtctccgggtgtcactcatgtgcccgctggggaagatgcgcctg
781   ---------+---------+---------+---------+---------+---------+   840
       E  V  A  T  T  S  L  R  V  S  L  M  C  P  L  G  K  M  R  L    -
                                              P
                                              s
                                              t
                                              I
      actgtcccatgccgcgctctcacctgtgcccacctgcagagtttcgatgctgccctttat
841   ---------+---------+---------+---------+---------+---------+   900
       T  V  P  C  R  A  L  T  C  A  H  L  Q  S  F  D  A  A  L  Y    - ctacagatgaatgagaaaaagccaacatggacgtgccctgtgtgtgacaagaaggctccc
901   ---------+---------+---------+---------+---------+---------+   960
       L  Q  M  N  E  K  K  P  T  W  T  C  P  V  C  D  K  K  A  P    - tatgagtcactgattattgatggtttattcatggaaattcttaattcctgttcggattgt
961   ---------+---------+---------+---------+---------+---------+  1020
       Y  E  S  L  I  I  D  G  L  F  M  E  I  L  N  S  C  S  D  C    -
                         P              B
                         f              a
                         l              m
                         M              H
                         I              I
      gatgagatccagttcatggaagatggatcctggtgtccaatgaaacccaagaaggaggca
1021  ---------+---------+---------+---------+---------+---------+  1080
       D  E  I  Q  F  M  E  D  G  S  W  C  P  M  K  P  K  K  E  A    -
                                              P
                                              f
                                              l
                                              M
                                              I
      tccgaggtttgccccccaccagggtatgggctggatggtctccagtatagcccagtccag
1081  ---------+---------+---------+---------+---------+---------+  1140
       S  E  V  C  P  P  P  G  Y  G  L  D  G  L  Q  Y  S  P  V  Q    - gagggaaatcagtcagagaataagaagagggttgaagtcattgacttgacaatcgaaagc
1141  ---------+---------+---------+---------+---------+---------+  1200
       E  G  N  Q  S  E  N  K  K  R  V  E  V  I  D  L  T  I  E  S    -
                   B
                   g
                   l
```

Figure 2 (continued)

```
                    I
                    I
      tcatcagatgaggaagatctgcccccaccaagaagcactgccctgttacctcggctgcc
1201 ---------+---------+---------+---------+---------+---------+ 1260
        S  S  D  E  E  D  L  P  P  T  K  K  H  C  P  V  T  S  A  A   -
                                                B
                                                s
                                                t
                                                E
                                                I
                                                I
      attccagcccttcctggaagcaaaggagccctgacctctggtcaccagccgtcttcggtg
1261 ---------+---------+---------+---------+---------+---------+ 1320
        I  P  A  L  P  G  S  K  G  A  L  T  S  G  H  Q  P  S  S  V   - ctgcggagccctgcaatgggtacactgggcagtgatttcctgtctagtctcccactacat
1321 ---------+---------+---------+---------+---------+---------+ 1380
        L  R  S  P  A  M  G  T  L  G  S  D  F  L  S  S  L  P  L  H   - gagtacccacctgccttcccgctgggggctgacatccaaggtttagatttatttttctttc
1381 ---------+---------+---------+---------+---------+---------+ 1440
        E  Y  P  P  A  F  P  L  G  A  D  I  Q  G  L  D  L  F  S  F   - cttcagactgagagtcagcactacagcccttcagttatcacttcactagatgagcaggac
1441 ---------+---------+---------+---------+---------+---------+ 1500
        L  Q  T  E  S  Q  H  Y  S  P  S  V  I  T  S  L  D  E  Q  D   -
                                              P
                                              f        A
                                              l        p
                                              M        a
                                              I        I
      accctt ggccact tcttccaattccggggaacccctccccacttcctgggcccactggcc
1501 ---------+---------+---------+---------+---------+---------+ 1560
        T  L  G  H  F  F  Q  F  R  G  T  P  P  H  F  L  G  P  L  A   - cccacattggggagctctcaccgcagcgccactccagcacccgctcctggccgtgtcagc
1561 ---------+---------+---------+---------+---------+---------+ 1620
        P  T  L  G  S  S  H  R  S  A  T  P  A  P  G  R  V  S   -
                                                              B
                                                              s
                                                              a
                                                              W
                                                              I
      agcattgtggctcctgggagttccttgagggaagggcatggaggacccctgccttccggt
1621 ---------+---------+---------+---------+---------+---------+ 1680
        S  I  V  A  P  G  S  S  L  R  E  G  H  G  G  P  L  P  S  G   -
```

Figure 2 (continued)

```
                                A
                                a
                                t
                                I
                                I
     ccctctttgactggctgtcggtcagacgtcatttccttggactga
1681---------+---------+---------+---------+-----  1725
     P   S   L   T   G   C   R   S   D   V   I   S   L   D   *   -
```

Enzymes that do cut:

| AatII | ApaI  | AvaI | BamHI | BglII | BsaWI | BstEII | EagI |
|-------|-------|------|-------|-------|-------|--------|------|
| HpaI  | PflMI | PstI | PvuII | StuI  |       |        |      |

Enzymes that do not cut:

| AgeI  | AseI  | BbrPI | BfrI    | BsaBI | BsmI    | BssHII | BstBI  |
|-------|-------|-------|---------|-------|---------|--------|--------|
| BstXI | ClaI  | DraI  | DraIII  | EcoRI | HindIII | KpnI   | MluI   |
| NarI  | NcoI  | NdeI  | NheI    | NotI  | NruI    | NsiI   | PmlI   |
| PvuI  | SacII | SalI  | SauI    | ScaI  | SfiI    | SmaI   | SnaBI  |
| SpeI  | SspI  | XbaI  | XhoI    |       |         |        |        |

Figure 3

```
                                                          A
                                                          p
                                                          a
                                                          I
    atgaagatcaaagagctttaccgacgacgctttccccggaagaccctggggccctctgat
1   ---------+---------+---------+---------+---------+---------+  60
    M  K  I  K  E  L  Y  R  R  R  F  P  R  K  T  L  G  P  S  D    - ctctcccttctctctttgcccctggcacctctcctgtaggctcccctggtcctctagct
61  ---------+---------+---------+---------+---------+---------+  120
    L  S  L  L  S  L  P  P  G  T  S  P  V  G  S  P  G  P  L  A    -

A
                                           p
                                           a
                                           I
    cccattcccccaacgctgttggcccctggcaccctgctgggccccaagcgtgaggtggac
121 ---------+---------+---------+---------+---------+---------+  180
    P  I  P  P  T  L  L  A  P  G  T  L  L  G  P  K  R  E  V  D    - atgcacccccctctgccccagcctgtgcaccctgatgtcaccatgaaaccattgcccttc
181 ---------+---------+---------+---------+---------+---------+  240
    M  H  P  P  L  P  Q  P  V  H  P  D  V  T  M  K  P  L  P  F    - tatgaagtctatggggagctcatccggcccaccacccttgcatccacttctagccagcgg
241 ---------+---------+---------+---------+---------+---------+  300
    Y  E  V  Y  G  E  L  I  R  P  T  T  L  A  S  T  S  S  Q  R    - tttgaggaagcgcactttacctttgccctcacaccccagcaagtgcagcagattcttaca
301 ---------+---------+---------+---------+---------+---------+  360
    F  E  E  A  H  F  T  F  A  L  T  P  Q  Q  V  Q  Q  I  L  T    - tccagagaggttctgccaggagccaaatgtgattataccatacaggtgcagctaaggttc
361 ---------+---------+---------+---------+---------+---------+  420
    S  R  E  V  L  P  G  A  K  C  D  Y  T  I  Q  V  Q  L  R  F    -
                      P
                      v
                      u
                      I
                      I
```

Figure 3 (continued)

```
    tgtctctgtgagaccagctgcccccaggaagattattttccccccaacctctttgtcaag
421 ---------+---------+---------+---------+---------+---------+ 480
    C  L  C  E  T  S  C  P  Q  E  D  Y  F  P  P  N  L  F  V  K   -
                               B
                               s
                               t
                               E
                               I
                               I
    gttaatgggaaactgtgcccccctgccgggttaccttcccccaaccaagaatggggccgag
481 ---------+---------+---------+---------+---------+---------+ 540
    V  N  G  K  L  C  P  L  P  G  Y  L  P  P  T  K  N  G  A  E   - cccaagaggcccagccgcccatcaacatcacacccctggctcgactctcagccactgtt
541 ---------+---------+---------+---------+---------+---------+ 600
    P  K  R  P  S  R  P  I  N  I  T  P  L  A  R  L  S  A  T  V   - cccaacaccattgtggtcaattggtcatctgagttcggacggaattactccttgtctgtg
601 ---------+---------+---------+---------+---------+---------+ 660
    P  N  T  I  V  V  N  W  S  S  E  F  G  R  N  Y  S  L  S  V   -
                                                              B
                      P                                       s
                      s                                       a
                      t                                       W
                      I                                       I
    tacctggtgaggcagttgactgcaggaacccttctacaaaaactcagagcaaagggtatc
661 ---------+---------+---------+---------+---------+---------+ 720
    Y  L  V  R  Q  L  T  A  G  T  L  L  Q  K  L  R  A  K  G  I   - cggaacccagaccactcgcgggcactgatcaaggagaaattgactgctgaccctgacagt
721 ---------+---------+---------+---------+---------+---------+ 780
    R  N  P  D  H  S  R  A  L  I  K  E  K  L  T  A  D  P  D  S   - gaggtggccactacaagtctccgggtgtcactcatgtgcccgctagggaagatgcgcctg
781 ---------+---------+---------+---------+---------+---------+ 840
    E  V  A  T  T  S  L  R  V  S  L  M  C  P  L  G  K  M  R  L   -
                                        P
                                        s
                                        t
                                        I
    actgtcccttgtcgtgccctcacctgtgcccacctgcagagcttcgatgctgcccttat
841 ---------+---------+---------+---------+---------+---------+ 900
    T  V  P  C  R  A  L  T  C  A  H  L  Q  S  F  D  A  A  L  Y   - ctacagatgaatgagaagaagcctacatggacatgtcctgtgtgtgacaagaaggctccc
901 ---------+---------+---------+---------+---------+---------+ 960
```

Figure 3 (continued)

```
         L   Q   M   N   E   K   K   P   T   W   T   C   P   V   C   D   K   K   A   P   -
             tatgaatctcttatcattgatggtttatttatggagattcttagttcctgttcagattgt
      961 ---------+---------+---------+---------+---------+---------+ 1020
         Y   E   S   L   I   I   D   G   L   F   M   E   I   L   S   S   C   S   D   C   -
                             P                   B
                             f                   a
                             l                   m
                             M                   H
                             I                   I
             gatgagatccaattcatggaagatggatcctggtgcccaatgaaacccaagaaggaggca
     1021 ---------+---------+---------+---------+---------+---------+ 1080
         D   E   I   Q   F   M   E   D   G   S   W   C   P   M   K   P   K   K   E   A   -
                                             P
                                             f
                                             l
                                             M
                                             I
             tctgaggtttgccccccgccagggtatgggctggatggcctccagtacagcccagtccag
     1081 ---------+---------+---------+---------+---------+---------+ 1140
         S   E   V   C   P   P   P   G   Y   G   L   D   G   L   Q   Y   S   P   V   Q   -
             ggggagatccatcagagaataagaagaaggtcgaagttattgacttgacaatagaaagc
     1141 ---------+---------+---------+---------+---------+---------+ 1200
         G   G   D   P   S   E   N   K   K   K   V   E   V   I   D   L   T   I   E   S   -
                                                                             P
                                                                             v
                                                                             u
                                                                             I
                                                                             I
             tcatcagatgaggaggatctgccccctaccaagaagcactgttctgtcacctcagctgcc
     1201 ---------+---------+---------+---------+---------+---------+ 1260
         S   S   D   E   E   D   L   P   P   T   K   K   H   C   S   V   T   S   A   A   -
             atcccggccctacctggaagcaaaggagtcctgacatctggccaccagccatcctcggtg
     1261 ---------+---------+---------+---------+---------+---------+ 1320
         I   P   A   L   P   G   S   K   G   V   L   T   S   G   H   Q   P   S   S   V   -
             ctaaggagccctgctatgggcacgttgggtggggatttcctgtccagtctcccactacat
     1321 ---------+---------+---------+---------+---------+---------+ 1380
         L   R   S   P   A   M   G   T   L   G   G   D   F   L   S   S   L   P   L   H   -
             gagtacccacctgccttcccactgggagccgacatccaaggtttagatttattttcattt
     1381 ---------+---------+---------+---------+---------+---------+ 1440
         E   Y   P   P   A   F   P   L   G   A   D   I   Q   G   L   D   L   F   S   F   -
             cttcagacagagagtcagcactatggcccctctgtcatcacctcactagatgaacaggat
```

Figure 3 (continued)

```
1441 ---------+---------+---------+---------+---------+---------+ 1500
         L  Q  T  E  S  Q  H  Y  G  P  S  V  I  T  S  L  D  E  Q  D    -
                                                                A
                                                                p
                                                                a
                                                                I
      gcccttggccacttcttccagtaccgagggacccccttctcactttctgggcccactggcc
1501 ---------+---------+---------+---------+---------+---------+ 1560
         A  L  G  H  F  F  Q  Y  R  G  T  P  S  H  F  L  G  P  L  A    -
                                       P              N
                                       s              a
                                       t              r
                                       I              I
      cccacgctggggagctcccactgcagcgccactccggcgccccctcctggccgtgtcagc
1561 ---------+---------+---------+---------+---------+---------+ 1620
         P  T  L  G  S  S  H  C  S  A  T  P  A  P  P  P  G  R  V  S    -
                                                          S
                                                          a
                                                          u
                                                          I
      agcattgtggcccctggggggggccttgagggaggggcatggaggacccctgccctcaggt
1621 ---------+---------+---------+---------+---------+---------+ 1680
         S  I  V  A  P  G  G  A  L  R  E  G  H  G  G  P  L  P  S  G    - ccctctttgactggctgtcggtcagacatcatttccctggactga
1681 ---------+---------+---------+---------+----- 1725
         P  S  L  T  G  C  R  S  D  I  I  S  L  D  *    -
```

Enzymes that do cut:

| ApaI | BamHI | BsaWI | BstEII | NarI | PflMI | PstI | PvuII |
|------|-------|-------|--------|------|-------|------|-------|
| SauI |       |       |        |      |       |      |       |

Enzymes that do not cut:

| AatII | AgeI    | AseI  | AvaI  | BbrPI | BfrI  | BglII   | BsaBI |
|-------|---------|-------|-------|-------|-------|---------|-------|
| BsmI  | BssHII  | BstBI | BstXI | ClaI  | DraI  | DraIII  | EagI  |
| EcoRI | HindIII | HpaI  | KpnI  | MluI  | NcoI  | NdeI    | NheI  |
| NotI  | NruI    | NsiI  | PmlI  | PvuI  | SacII | SalI    | ScaI  |
| SfiI  | SmaI    | SnaBI | SpeI  | SspI  | StuI  | XbaI    | XhoI  |

Figure 4

```
  1 MKIKELYRRRFPRKTLGPSDLSLLSLPPGTSPVGSPGPLAPIPPTLLAPG  50
    ||||||||||||||||||||||||||||||||||:|||.||||||.||
  1 MKIKELYRRRFPRKTLGPSDLSLLSLPPGTSPVGSPSPLASIPPTLLTPG  50

51 TLLGPKREVDMHPPLPQPVHPDVTMKPLPFYEVYGELIRPTTLASTSSQR 100
    |||||||||||||||||||||||||||||||||||||||||||||||||
 51 TLLGPKREVDMHPPLPQPVHPDVTMKPLPFYEVYGELIRPTTLASTSSQR 100

101 FEEAHFTFALTPQQVQQILTSREVLPGAKCDYTIQVQLRFCLCETSCPQE 150
    ||||||||||||||:||||||||||||||||||||||||||||||||||
101 FEEAHFTFALTPQQLQQILTSREVLPGAKCDYTIQVQLRFCLCETSCPQE 150

151 DYFPPNLFVKVNGKLCPLPGYLPPTKNGAEPKRPSRPINITPLARLSATV 200
    |||||||||||||||||||||||||||||||||||||||||||||||||
151 DYFPPNLFVKVNGKLCPLPGYLPPTKNGAEPKRPSRPINITPLARLSATV 200

201 PNTIVVNWSSEFGRNYSLSVYLVRQLTAGTLLQKLRAKGIRNPDHSRALI 250
    |||||||||||||||||||||||||||||||||||||||||||||||||
201 PNTIVVNWSSEFGRNYSLSVYLVRQLTAGTLLQKLRAKGIRNPDHSRALI 250

251 KEKLTADPDSEVATTSLRVSLMCPLGKMRLTVPCRALTCAHLQSFDAALY 300
    |||||||||||||||||||||||||||||||||||||||||||||||||
251 KEKLTADPDSEVATTSLRVSLMCPLGKMRLTVPCRALTCAHLQSFDAALY 300

301 LQMNEKKPTWTCPVCDKKAPYESLIIDGLFMEILSSCSDCDEIQFMEDGS 350
    |||||||||||||||||||||||||||||||||||.|||||||||||||
301 LQMNEKKPTWTCPVCDKKAPYESLIIDGLFMEILNSCSDCDEIQFMEDGS 350

351 WCPMKPKKEASEVCPPPGYGLDGLQYSPVQGGDPSENKKKVEVIDLTIES 400
    |||||||||||||||||||||||||||||:|:.||||:|||||||||||
351 WCPMKPKKEASEVCPPPGYGLDGLQYSPVQEGNQSENKKRVEVIDLTIES 400

401 SSDEEDLPPTKKHCSVTSAAIPALPGSKGVLTSGHQPSSVLRSPAMGTLG 450
    ||||||||||||.||||||||||||||||.|||||||||||||||||||
401 SSDEEDLPPTKKHCPVTSAAIPALPGSKGALTSGHQPSSVLRSPAMGTLG 450

451 GDFLSSLPLHEYPPAFPLGADIQGLDLFSFLQTESQHYGPSVITSLDEQD 500
    :||||||||||||||||||||||||||||||||||||:|||||||||||
451 SDFLSSLPLHEYPPAFPLGADIQGLDLFSFLQTESQHYSPSVITSLDEQD 500

501 ALGHFFQYRGTPSHFLGPLAPTLGSSHCSATPAPPPGRVSSIVAPGGALR 50
    .||||||:||||.||||||||||||| ||||||:|||||||||||:.||
501 TLGHFFQFRGTPPHFLGPLAPTLGSSHRSATPAPAPGRVSSIVAPGSSLR 550

551 EGHGGPLPSGPSLTGCRSDIISLD* 575
    |||||||||||||||||||:|||||
551 EGHGGPLPSGPSLTGCRSDVISLD* 575
```

PROTEIN THAT ENHANCES EXPRESSION OF POTASSIUM CHANNELS ON CELL SURFACES AND NUCLEIC ACIDS THAT ENCODE THE SAME

BACKGROUND OF THE INVENTION

The electrical properties of excitable cells are determined in large part by the voltage-gated $K^+$ channels, i.e., "Kv channels", present on the plasma membrane of such cells. Kv channels are also important in many nonexcitable cells where they contribute to diverse processes such as volume regulation, hormone secretion, and activation by mitogens. At least 50 different Kv channel genes have been identified, and most have been assigned to one of the following four major subfamilies: Kv1, Kv2, Kv3, and Kv4. Each Kv channel gene encodes a single pore-forming subunit, referred to as the α-subunit. Functional Kv channels are formed by the tetrameric association of individual α-subunits. With multiple Kvα proteins that assemble as multi-subunit heteromeric complexes, there may be hundreds of functionally distinct Kv channels.

Kv channels, either functioning or malfunctioning, are implicated in many disease states including cardiac arrhythmias, hypertension, angina, asthma, diabetes, renal insufficiency, urinary incontinence, irritable colon, epilepsy, cerebrovascular ischemia and autoimmune diseases Accordingly, efforts are underway to identify and characterize pharmacological agents that alter the kinetics, gating or formation of Kv channels. The efficacy of such agents is determined by treating cells with such agents and measuring changes in current across the plasma membrane of the cells. Unfortunately, it is difficult to measure small changes in the current in most cells. It is also difficult to determine whether a pharmocological agent alters current flow through a specific Kv channel. Accordingly, it is desirable to have methods and tools which can be used to regulate the numbers and types of Kv channels on the plasma membrane of cells. It is also desirable to have new research tools that can be used for examining the assembly and synthesis of Kv channels.

SUMMARY OF THE INVENTION

The present invention provides novel polynucleotides that encode a novel protein, designated herein as K+ Channel Associated Protein or "KChAP". It has been determined that expressing polynucleotides that encode KCHAP in host cells, along with polynucleotides that encode the Kvα channel subunit Kv 2.1, the Kvα channel subunit Kv 2.2, the Kvc channel subunit Kv 1.3, or the Kvα channel subunit Kv 4.3, increases the number of Kv2.1, Kv 2.2, Kv1.3 or Kv4.3 channels, respectively, in the plasma membrane of such cells. Accordingly, KChAP polynucleotides are useful for making cells that have increased numbers of Kv channels on the cellular plasma membrane. Such cells are useful model systems for studying the effect of pharmacological agents on Kv channels, particularly on Kv2.1, Kv 2.2, Kv 1.3, and Kv 4.3 channels.

The present invention also relates to the novel protein KChAP. During formation of Kv channels, KChAP binds to the Kvx channel subunits Kv2. 1, Kv2.2, Kv1.3, and Kv4.3 within the cytoplasm of the cell. KChAP also binds to the Kvα channel subunits Kv1.2, Kv 1.4, Kv1.5 and Kv 3.1 and to Kvβ subunits. Accordingly, KChAP and the antibodies that are immunospecific for KChAP are useful research tools for monitoring the interaction between diverse Kvx channel subunits and KCHAP and for monitoring the interaction between Kvα subunits and Kvα subunits.

BRIEF DESCRIPTION OF THE FIGURES

FIG. 2 shows a cDNA sequence, SEQ ID NO: 1, that encodes rat KCHAP, and the predicted amino acid sequence, SEQ ID NO: 2, of the KChAP protein encoded by the rat cDNA;

FIG. 3 shows a cDNA sequence, SEQ ID NO: 3, that encodes human KChAP, and the predicted amino acid sequence, SEQ ID NO: 4, of the KChAP protein encoded by the human cDNA;

FIG. 4 provides a comparison of the amino acid sequences of rat KChAP and human KChAP. The double dots between the sequences identify highly conserved amino acids, i.e., amino acids that are similar in size, hydrophobicity, and charge. The single dot between the aligned amino acid sequences identify amino acids that are less highly conserved.

DETAILED DESCRIPTION OF THE INVENTION

The KCHAP Protein

Figure 1:
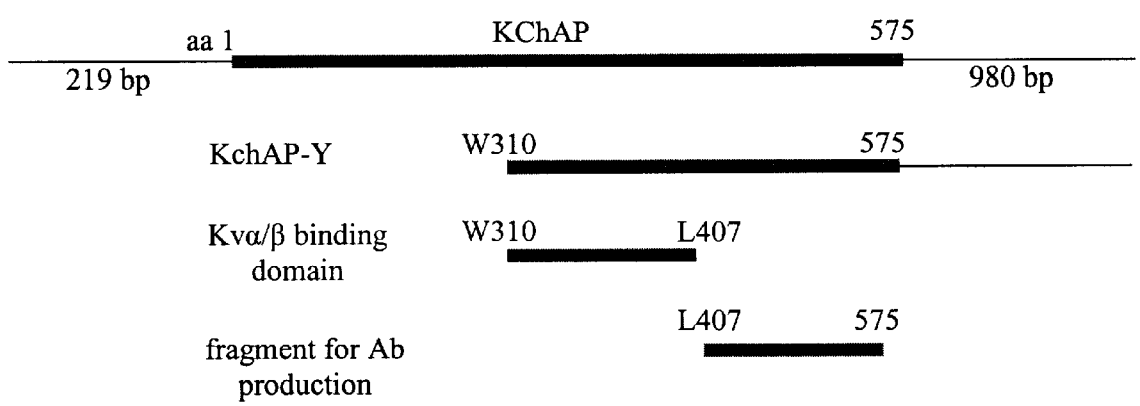
FIG. 1 is a schematic representation of a full-length cDNA that encodes KChAP and partial fragments thereof. The open reading frame is flanked by 219 base pairs of untranslated sequence on the 5' end, and 980 base pairs of untranslated sequence on the 3' end as indicated by the thin lines. KChAP-Y depicts the partial clone that was originally isolated in the yeast two-hybrid screen. KChAP-Y extends from amino acid W310 through the poly A tail at the 3' end. The domain on KCHAP that binds to Kvα subunits and to Kvβ subunits, hereinafter referred to as the "Kvα/Kvβ "binding domain", has been localized to the region between amino acids W310 and L407.

The present invention provides a unique protein KChAP. The mature form of KChAP has a calculated molecular weight of about 62.4 kDa. In one embodiment the human KChAP protein has the amino acid sequence shown in FIG. 3 (SEQ ID NO: 4). In one embodiment the rat KChAP protein has the amino acid sequence shown in FIG. 2 (SEQ ID NO: 2).

The present invention also relates to allelic variants or derivatives of the amino acid sequences shown in FIGS. 2 and 3. In addition to naturally occurring allelic forms of the protein, the KChAP protein as described herein embraces non-naturally occurring derivatives of the KChAP protein where one or more of the amino acids have been replaced by conservative amino acid residues, typically by using direct synthesis or recombinant techniques. The present invention also relates to allelic variants or derivatives of the KChAP that have an amino acid sequence identity of at least 85%, more preferably at least 90%, and most preferably of at least 95% with the amino acid sequences shown in FIG. 2 or FIG. 3, provided however, that the derivative is capable of binding to the N-ternini of the Kvα subunits Kv 2.1, Kv2.2, Kv 1.3, Kv4.3 and to the C-terminus of Kvβ 1.2.

In another aspect, the present invention relates to an isolated peptide which comprises the domain of KChAP that binds to Kvα subunits, particularly the Kvα subunits Kv 2.1, Kv2.2, Kv4.3 and to Kvβ subunits, particularly Kvβ 1.2. Such domain is hereinafter referred to as the "Kvα/Kvβ binding domain". As used herein, peptide means a fragment of the KCHAP protein and accordingly is smaller and comprises fewer amino acids than the KCHAP protein. In one embodiment, this peptide comprises the amino acid sequence, SEQ ID NO: 5, extending from T309 through L407 as shown in FIG. 2 and the amino acid sequence, SEQ ID NO: 7, extending from T309 through L407 as shown in FIG. 3. The present invention also relates to allelic variants or derivatives of the amino acid sequence set forth in SEQ ID NO's: 5 and 7.

In another aspect, the present invention relates to an isolated peptide which comprises the C terminal domain of the KChAP protein, i.e., the last 160 to 170 amino acids of the KChAP protein. In one embodiment, the peptide comprises the amino acid sequence set forth in SEQ ID NO: 8 In another embodiment, the peptide comprises the amino acid sequence set forth in SEQ. ID NO: 9. In another embodiment, the peptide is a variant of the C terminal domain of the rat KChAP protein and the human KChAP protein and comprises:

(a) a Kvα/Kvβ binding domain having the following sequence:
WTCPVCDKKA PYESLIIDGL FMEILXaSCSD CDEIQFMEDG SWCPMKPKKE ASEVCPPPGY GLDGLQYSPV QXaGXaXaSENKK XAVEV-IDLTIE SSSDEEDL, SEQ ID NO: 10,
wherein the Xa at position 25 is serine or asparagine, the Xa at position 72 is glycine or glutamic acid, the Xa at position 74 is aspartic acid or asparagine, the Xa at position 75 is proline or glutamine the Xa at position 80 is lysine or arginine; and (b) a C terminal domain having the following sequence:
PPTKKHCXaVT SAAIPALPGS KGXALTSGHQP SSVLRSPAMG TL GXaDFLSSL PLHEYPPAFP LG ADIQGLDL FSFLQTESQH YXaPSVITSLD EQDXaLGHFFQ XaRGTPXaHFLG PLAPTLGSSH XaS ATPAPXaPG RVSSIVAPGXa XaLREGHGGPL PSGPSLTGCR SDIXaSLD SEQ ID NO: 11;
wherein the Xa at position 8 is serine or proline, the Xa at position 23 is valine or alanine, the Xa at position 44 is glycine or serine, the Xa at position 82 is, glycine or serine, the Xa at position 94 is alanine or threonine, the Xa at position 101 is tyrosine or phenylalanine, the Xa at position 106 is serine or proline, the Xa at position 121 is cystine or arginine, the Xa at position 128 is proline or alanine, the Xa at position 140 or glycine or serine, the Xa at position 141 is alanine or serine, the Xa at position 164 is isoleucine or valine.

Such peptides are useful for producing antibodies that are immunospecific for KChAP.

The present invention also relates to fusion proteins wherein additional amino acids are fused to the KChAP protein or to the peptide fragments of KChAP. The additional amino acids are added at either the 3' end or 5' end of the protein or peptide, for example, to aid in purification of the protein or peptide. The KChAP proteins and peptides are provided in an isolated form. KChAP is not a channel protein. KChAP binds with the N-termini of Kvα1 and Kvα2 subunits. Specifically, KChAP binds with the a subunits Kv 2.1, Kv 2.2, Kv 1.3, Kv 4.3, Kv1.2, Kv1.4, Kv1.5. KChAP also binds to Kvα subunits, particularly Kvα1 and its isoforms. Kvβ subunits are cytoplasmic proteins that form stable complexes with Kvα1 subunits. Kvβ subunits are strong modulators of Kv channels. The Kvβ subunit, Kvβ1.2 suppresses current in the Kv1.5 potassium channel; this effect is abolished by KChAP which binds the Kvp1 .2.

Preparing KChAP

KChAP may be synthetically produced by conventional peptide synthesizers. Preferably, KChAP is produced using cell-free translation systems and RNA molecules derived from DNA constructs that encode the KCHAP protein. Alternatively, KChAP is made by transfecting host cells with expression vectors that comprise a DNA sequence that encodes the KCHAP protein and then inducing expression of the protein in the host cells. For recombinant production, recombinant constructs comprising one or more of the sequences which encode KChAP are introduced into host cells by conventional methods such as calcium phosphate transfection, DEAE-dextran mediated transfection, transvection, microinjection, cationic lipid-mediated transfection, electroporation, transduction, scrape lading, ballistic introduction or infection.

KChAP is expressed in suitable host cells, such as for example, mammalian cells, yeast, bacteria, or other cells under the control of appropriate promoters using conventional techniques. Following transformation of the suitable host strain and growth of the host strain to an appropriate cell density, the cells are harvested by centrifugation, disrupted by physical or chemical means, and the resulting crude extract retained for further purification of the KChAP protein.

Conventional procedures for isolating recombinant proteins from transformed host cells, such as isolation by initial extraction from cell pellets or from cell culture medium, followed by salting-out, and one or more chromatography steps, including aqueous ion exchange chromatography, size exclusion chromatography steps, high performance liquid chromatography (HPLC), and affinity chromatography may be used to isolate recombinant KChAP.

Preparation of Antibodies

Recombinant KChAP or portions thereof, i.e., KChAP peptides, are used as immunogens to produce antibodies immunospecific for wild-type KChAP. Preferably, the KChAP peptides have little sequence homology with the human Gu binding protein, whose amino acid sequence is about 50% homologous with the amino acid sequences shown in FIGS. 2 and 3. The term "immunospecific" means the antibodies have substantially greater affinity for KChAP than for other proteins. Such antibodies are generated using conventional techniques by administering KChAP or the portion thereof to an animal, preferably a nonhuman, more preferably a rabbit. Conventional protocols are also used to collect blood from the immunized animals and to isolate the serum and or the IgG fraction from the blood. For preparation of monoclonal antibodies, conventional hybridoma techniques are used.

Polyclonal serum to KChAP was made using a bacterial fusion protein comprising the C-terminal 167 amino acids of KChAP. i.e., from amino acid L407, fused to the maltose binding protein. The fusion protein was prepared by subdloning the C-terminal 167 amino acids of KChAP into pMAL-C2 vector from New England Biolabs. The resulting vector was used to transform *E. coli*. The fusion protein was isolated from transformed *E. coli* cells on an amylose resin and sent to Research Genetics, Inc. for generation of polyclonal sera using conventional techniques Antibodies to KChAP are useful analytical tools for monitoring the formation of Kv channels and for studying the intracellular association of KChAP with Kvα subunits and with Kvα subunits. Such antibodies are also useful reagents for identifying the intracellular location of the interaction between KChAP and Kvα and Kvβ subunits. Such antibodies are also useful to isolate or identify cells expressing the KCHAP protein and to purify KChAP from partially purified preparations by affinity chromatography.

The KChAP Polynucleotide

The present invention also provides polynucleotides that encode the KChAP protein and the KChAP peptides of the present invention, hereinafter referred to collectively as the "KChAP polynucleotides". The KChAP polynucleotide is single stranded or double stranded. The polynucleotide is a DNA or RNA molecule, preferably a DNA molecule, and comprises a sequence which codes for the KChAP protein, preferably the human KChAP protein, or fragments thereof. Optionally, the polynucleotide also comprises a leader sequence and encodes a KCHAP protein which is processed and secreted from mammalian cells as the mature polypeptide. Polynucleotides encoding KChAP protein may also be fused in frame to a marker sequence which allows for purification of the KChAP protein such as the maltose binding protein, which binds to amylose resin. Polynucleotides encoding KCHAP protein or KChAP peptide fragments may also be fused in frame to a marker sequence, such as c-myc, which encodes an epitope that allows for monitoring the intracellular location of KChAP using commercially available antibodies.

In one embodiment, the KChAP polynucleotide encodes for a KCHAP protein comprising the amino acid sequence shown in FIG. 2, SEQ ID NO: 2. One example of a polynucleotide that encodes the protein of SEQ ID NO: 2, is depicted in FIG. 2, and set forth in SEQ ID NO: 1. In another embodiment, the polynucleotide encodes for a KChAP protein comprising the amino acid sequence shown in FIG. 3, SEQ ID NO: 4. One example of a polynucleotide that encodes the protein of SEQ ID NO: 4 is depicted in FIG. 3 and set forth in SEQ ID NO: 3. The present invention also relates to polynucleotides that encode an allelic variant of the proteins having the amino acid sequences shown in FIGS. 2 and 3.

In another embodiment, the polynucleotide encodes for variants of KChAP protein, wherein the variants have the following sequence:
MKIKELYRRR FPRKTLGPSD LSLLSLPPGT SPVG-SPXAPLA XaIPPTLLXaPG TLLGPKREVD MHP-PLPQPVH PDVTMKPLPF YEVYGELIRP TTLASTSSQR; FEEAHFTFAL TPQQXaQQILT SREV-LPGAKC DYTIQVQLRF CLCETSCPQE; DYFPPN-LFVK VNGKLCPLPG YLPPTKNGAE PKRPSRPINI TPLARLSATV; PNTIVVNWSS EFGRNYSLSV YLVRQLTAGT LLQKLRAKGI RNPDHSRALI; KEK-LTADPDS EVATTSLRVS LMCPLGKMRL TVPCRALTCA HLQSFDAALY; LQMNEKKPTW TCPVCDKKAP YESLIIDGLF MEILXaSCSDC DEIQFMEDGS; WCPMKPKKEA SEVCPPPGYG LDGLQYSPVQ XaGXaPSENKKXa VEVIDLTIES; SSDEEDLPP TKKHCXaVTSA AIPALPGSKG XaLTS-GHQPSS VLRSPAMGTLG; XaDFLSSLPLH EYPPAF-PLGA DIQGLDLFSF LQTESQHYXaP SVITSLDEQD; XaLGHFFQXaRG TPXaHFLGPLA PTLGSSHXaSA TPAPXAPGRVS SIVAPGXaXaLR; EGHGGPLPSG PSLTGCRSDI XaSLD, SEQ ID NO: 6;

wherein the amino acid Xa at position 37 is glycine or serine;
the amino acid Xa at position 41 is proline or serine;
the amino acid Xa at position 48 is alanine or threonine;
the amino acid Xa at position 115 is valine or leucine;
the amino acid Xa at position 335 is serine or asparagine;
the amino acid Xa at position 381 is glycine or glutamic acid;
the amino acid Xa at position 383 is aspartic acid or asparagine;
the amino acid Xa at position 384 isoproline or glutamine;
the amino acid Xa at position 390 is lysine or arganine;
the amino acid Xa at position 416 is serine or proline;
the amino acid Xa at position 431 is valine or alanine;
the amino acid Xa at position 451 is glycine or serine;
the amino acid Xa at position 489 is glycine or serine;
the amino acid Xa at position 501 is alanine or threonine;
the amino acid Xa at position 508 is tyrosine or phenylalanine;
the amino acid Xa at position 513 is serine or proline;
the amino acid Xa at position 528 is cysteine or arginine
the amino acid Xa at position 535 is proline or alanine;
the amino acid Xa at position 547 is glycine or serine;
the amino acid Xa at position 548 is alanine or serine;
the amino acid Xa at position 570 is isoleucine or valine.

The present invention further relates to polynucleotides which are complementary to sequences that have at least 85% identity, preferably 90% identity, more preferably 95% identity with the nucleotide sequences which encode the amino acid sequences shown in FIGS. 2 and 3 or SEQ ID NO: 6.

Preferably, the polynucleotides comprise a sequence which hybridizes under stringent conditions to sequences which encode the amino acid sequence shown in FIG. 2 and FIG. 3 or sequences which are complementary thereto. As herein used, the term "stringent conditions" means hybridization will occur if there is at least 95% and, preferably, at least 97% identity between the sequences. Preferably, the polynucleotide is provided in an isolated form.

The polynucleotides that encode the KChAP protein are useful for preparing cells that have increased numbers of Kv channels on their cell surface. The polynucleotides of the present invention are useful for preparing cells that have Kv channels formed from exogenous Kvα subunits. As used herein, "an exogenous Kvα subunit" means that the gene encoding the Kvα subunit is not normally expressed in the cell. Kvα subunits that are normally expressed in a cell are referred to as endogenous subunits. To prepare the cells, polynucleotides encoding KChAP and a Kvα subunit, an exogenous Kvx subunit, preferably are co-transfected or co-injected into host cells. Preferably, the cRNA molecules that encode KChAP and the Kvx subunit are coinjected with one pipette. Preferably, the Kvα subunit is a Kv2.1, Kv2.2, Kv1.3 or Kv4.3 subunit, The resulting cells, which have on the surface thereof increased numbers of Kv channels formed by the exogenogous Kvα subunits, are useful for testing the efficacy of compounds designed to alter current flow through the newly-expressed Kv channels such as, for example by measuring whole-cell currents using the conventional two microelectrode voltage-clamp technique.

The KChAP polynucleotides are also useful for producing KChAP constructs which are useful for producing KChAP protein or fragments thereof by recombinant techniques. Such constructs include, among others, vectors, such as a plasmid, phagemid, or viral vector, into which a sequence that encodes the KChAP protein has been inserted. Optionally, such constructs encode a fusion KChAP which includes an N-termninal or C-terminal peptide or tag that simplifies purification of the expressed recombinant product. Representative examples of such tags include sequences which encode a series of histidine residues, the Herpes simplex glycoprotein D, or glutathione S-transferase.

Polynucleotides encoding KChAP are also useful for designing hybridization probes for isolating and identifying cDNA clones and genomic clones encoding KChAP, or for identifying cells and tissues containing KCHAP transcripts. Such hybridization techniques are known to those of skill in the art. Sequence of polynucleotides that encode human or rat KCHAP are also useful for designing primers for polymerase chain reaction, a technique useful for obtaining large quantities of cDNA molecules that encode KChAP.

Preferably, the primers comprise 18–30 nucleotides, more preferably 19–25 nucleotides. Preferably, the primers have a G+C content of 40% or greater.

Cloning the C Terminal Region of a cDNA that Encodes Rat KCHAP

A cDNA encoding the C terminal region of rat KChAP was isolated using the Yeast Two-Hybrid Library Screen and a rat brain cDNA library in the GAL4 activation domain vector, pGAD10, obtained from Clontech. In this procedure the entire coding sequence of Kvβ1.2 (amino acids 1–408), which was used as bait for proteins that interact with Kvβ1.2, was subdloned in frame into the GAL4 DNA binding domain vector, pGBT9 from Clontech after PCR-mediated addition of a 5' EcoRI site and a 3' SalI site. The yeast Y190 strain (with two reporter genes, lacZ and HIS3) was cotransformed simultaneously with Kvβ1.2 pGBT9 and pGAD10 library DNA, and plated on synthetic medium lacking tryptophan (trp), leucine (leu), and histidine (his) plus 3-aminotriazole (25 mm) to prevent leaky transcription of the HIS3 gene. After incubation for 8 days at 30° C., His colonies were screened for β-galactosidase activity by a filter lift assay as outlined in Clontech protocols. Yeast DNA was isolated from colonies positive for both reporter genes using a phenol/glass-bead protocol (Clontech). Individual library plasmids were isolated after transformation of yeast DNA into chemically competent HB101 bacteria and growth on minimal medium lacking leucine. Individual pGAD10 recombinant plasmids were screened for interaction with Kvβ1.2 by repeating the yeast two-hybrid assay in Y190 cells. One plasmid, designated herein as the "KCHAP-Y plasmid", activated transcription -of the reporter genes in cells co-transformed simultaneously with Kvβ1.2 pGBT9, but did not activate transcription in control cells transformed with the KChAP-Y plasmid alone.

KCHAP-Y plasmid cDNA was sequenced, and found to comprise a 1.78 kb insert encoding an open reading frame of 264 amino acids and 980 base pairs of 3' untranslated sequence including the poly (A$^+$) tail. This insert or fragment is designated herein as "KCHAP-Y".

Cloning of a Full-Length cDNA Encoding rat KChAP

A polynucleotide encoding KChAP-Y was used as a probe to obtain a full-length cDNA encoding KChAP. In this procedure, the $^{32}$P labeled KChAP-Y insert was used to screen a rat brain cDNA library in λgt10 from Clontech. One of the hybridizing clones contained an insert of 3.2 kb with a single open reading frame encoding a protein of 574 amino acids. The start methionine was identified as the first ATG downstream from three in frame stop codons.

The full length cDNA encoding KChAP, designated herein as the "KChAP gene" is shown schematically in FIG. 1. The sequence of the KCHAP gene is shown in FIG. 2 and set forth in SEQ ID NO: 1. Hydropathy analysis showed no putative membrane spanning regions in KCHAP. The open reading frame of the KChAP gene predicts a protein of 574 amino acids and having the sequence shown in FIG. 2, SEQ ID NO: 2. The open reading frame of the KChAP gene is flanked by 219 base pairs of untranslated sequence on the 5' end, and 980 base pairs of 3' untranslated sequence. The 980 base pair sequence as indicated by the thin lines in FIG. 1. The Kvα/Kvβ binding domain on the KChAP gene has been localized to the region which encodes amino acids W310 through L407. The Kvαx/Kvp binding domain has the amino acid sequence set forth in SEQ ID NO: 5. KChAP-Y extends from amino acid W310 of the full-length KChAP protein through the poly A tail at the 3' end.

In Vitro Transcription and Translation of the KChAP Gene

Full-length KChAP cDNA was removed from pGBT9 with EcoRI and SalI and subcloned into a pCR3 vector which was modified to allow the cloning of EcoRI/SalI fragments in frame behind a c-myc tag. The KChAP fragment for subcloning was prepared by PCR to contain only a consensus Kozak sequence at the 5' end and a poly (A$^+$) tail just past the stop codon at the 3' end to eliminate most of the 5' and 3' untranslated sequences in the expression construct. KChAP cRNA was prepared using the T7 MMESSAGE MMACHINE kit (Ambion) following linearization of the construct with NotI. cRNA for c-myc-KChAP was translated in vitro in a rabbit reticulocyte lysate to provide the fusion protein c-myc-KChAP. Cloning of a Full-Length cDNA Encoding Human KChAP Reverse transcriptase and polymerase chain reaction (RT-PCR) techniques were used to clone a cDNA encoding human KChAP. The template was human brain poly A+ RNA from Clonetech. The reverse transcription reaction mixture was incubated for 1 hour at 42° C., and then heat inactivated.

PCR amplification was performed using the sense primer 5'ATGAAGATCAAAGAGCTTTACCGACG 3', SEQ ID NO: 12 and the antisense primer 5'TCAGTCCAGG-GAAATCATGACCG 3', SEQ ID NO: 13, which flank the start methionine and stop codon, respectively. The following reagent concentrations were used for amplification: 5% DMSO, 0.2 mM of each dNTP, 0.2 pmole/ μl of each oligomeric primer, Clonetech's Advantage cDNA polymerase mix and buffer. The cycling protocol was as follows: one cycle at 94° C. for 2 minutes; 35 cycles at 94° C. for 15 seconds, 50° C. for 15 seconds, and 72° C. for 30 seconds; and one cycle at 72° C. for 10 minutes.

The PCR product was gel-purified using Qiaquick Gel Extraction Kit from Qiagen, subcloned into PCRII from Invitrogen and sequenced using Sequenase from U.S. Biochemicals. The nucleotide sequence of the open reading frame, SEQ ID NO: 3, and the predicted amino acid sequence, SEQ ID NO: 4, encoded thereby are shown in FIG. 3.

Increasing the Number of Kv2.1, 2.2. 1.3 and 4.3 Channels in Host Cells

A. Materials

Human Gu binding protein cDNA encoding the peptide spanning amino acids M49 to D645 was obtained by RT-PCR from human brain poly A+ RNA and subcloned into pCRII (Invitrogen) for transcription. A Kozak sequence was included in the 5' oligo to facilitate translation in oocytes. cRNAs for Kvlax-subunits were prepared as described in Majumder et al, (1995), FEBS Letts, 377, 383–389, and Wang et al. (1996), J. Bio. Chem., 271, 28311–28317. cRNA encoding Kv2.1ΔN (in which the N-terminal 139 amino acids had been deleted) prepared was as described in Van-Dongen et al, (1990), Neuron 5, 433–443. HERG cDNA was obtained from Dr. M. Keating. Kv2.2 was obtained from Drs. S. Snyder and J. Trimmer. Rat Kv2.1 in pBluescript was linearized with NotI and cRNA was prepared with T7 polymerase. cRNA concentrations were estimated on denaturing agarose gels stained with ethidium bromide by comparison with RNA standards. cRNAs were mixed and injected into Xenopus oocytes as described in Majumder et al, (1995).

B. Methods

Xenopus oocytes were co-injected with cRNA molecules encoding human KChAP protein or rat KChAP protein and with cRNA molecules encoding one of the following Kvα subunits: Kv1.2, Kv1.5, Kv3.1, Kv2.1, Kv2.2 and Kv4.3, or with cRNA molecules encoding Kir 2.2, HERG, and Kv2.1ΔN. As a control, Xenopus oocytes were injected with cRNA molecules encoding the a-subunits alone. For comparison Xenopus oocytes were co-injected with cRNA molecules encoding human Gu binding protein and the a-subunits.

Whole oocyte currents were measured either two days after co- injection of c-myc-KchAP cRNA and cRNAs encoding Kv4.3, Kv1.2, Kv3.1, Kir 2.2, or aKv2.1ΔN, or five days post-injection from oocytes injected with cRNAs encoding Kv2.1, Kv2.2, Kv1.5 or HERG plus c-myc- KChAP cRNA. Bath solution contained (in mmol/liter): 5 KOH, 100 NaOH, 0.5 $CaCl_2$, 2 $MgCl_2$, 100 MES, and 10 HEPES (pH 7.4). Solution containing 50 $K^+$ was prepared by replacing an equivalent concentration of $Na^+$. Electrodes were filled with 3 M KCl and had a resistance of 0.3–0.6 MΩ. All recordings were made at room temperature. Linear leakage and capacity transient currents were subtracted (P/4 prepulse protocol) unless specified and data were low pass filtered at 1 kHz. pClamp software (Axon Instruments) was used for generation of the voltage-pulse protocols and data acquisition. Means ±S.E.M. were calculated and were considered to be significantly different when P<0.05. Comparisons among multiple groups of oocytes were performed by one-way ANOVA test and Student-Newman-Keuls post-hoc test (SKN test).

For Kv1.2, Kv1.5, Kv2.1, Kv2.1ΔN, Kv2.2 Kv3.1 and Kv4.3 channels holding potential was −80 mV. Peak (Kv4.3) or steady state (other channels) currents were measured at a test potential of +70 mV (5 or 50 K+ in the bath). Kir 2.2 and HERG currents were recorded with 50 K+ in the bath at test potential to −100 mv with a pre-pulse to +20 mV.

The results indicated that co-injection of oocytes with cRNA encoding KChAP and encoding either Kv2. 1 α subunit, or Kv2.2 α subunit, or Kv4.3 α subunit significantly increased the amplitude of Kv2.1, Kv2.2, and Kv4.3 currents as compared to oocytes injected with these respective α-subunits alone. No change was observed in the currents of control oocytes or oocytes coinjected with cRNA encoding KChAP and cRNA encoding either Kv1.2 a subunit, or Kv1.5 a subunit, or Kv3.1α subunit. The results also indicated that KChAP did not alter the kinetics or gating of Kv2.1, Kv2.2, or Kv4.3 channels.

Several hours after recording, the oocytes injected with cRNA molecules encoding KChAP and Kv2.2 a subunit were fixed in 4% paraformaldehyde. 50 μ vibrotome sections were cut, and incubated for 2 hours in 1% BSA/PBS to block nonspecific binding sites. The sections were incubated at 4° C. overnight in primary antibodies, that is an anti-Kv2.1 α subunit, rabbit polyclonal antibody, from Upstate Biotechnology, Inc.; and anti-c-myc, a mouse monoclonal antibody, from Boehringer Mannheim, Inc. The sections were washed, and incubated for 2 hours at room temperature in secondary antibodies, FITC-conjugated anti-rabbit for Kv2.1 and TRITC-conjugated anti-mouse for c-myc. Sections were examined with an Olympus BH-2 microscope for the appearance of fluorescence.

The FITC fluorescence, which indicates the amount of Kv2.1 α subunit, was much brighter at the oocyte surface in eggs expressing both Kv2.1 and KChAP as compared to eggs expressing the Kv2.1 α subunit alone. Thus, co-injection cRNA molecules encoding KChAP with cRNA encoding either Kv2.1, Kv2.2, or Kv4.3 α subunits increases the number of functional Kv2.1, Kv2.2 and Kv4.3 channels on the plasma membrane of cells as compared to cells injected with cRNA molecules encoding the Kvα subunits alone. By increasing the number of functional Kv2.1, Kv2.2 and Kv4.3 channels on the surface of a host cell, one can more readily study the channels and more easily observe the effect of pharmaceutical agents on such channels.

Interaction of KCHAP with Kvα and Kvβ Subunits.

The interaction of KChAP with particular Kvα and β subunits was examined using an indirect and direct procedure.

(a) Indirect Procedure for Monitoring Interaction of KChAP with Kvα and Kvβ subunits In the indirect procedure, the yeast Matchmaker Two-Hybrid System Clontech and cDNA molecules encoding KChAP and KChAP-Y were used. The binding specificity between full length KChAP or KChAP-Y and the following Kvα, Kvβ and other K+ channel subunit fragments were determined: Kvβ1.2 (amino acids 1–408), Kvβ1.2-N terminus (amino acids 1–79), Kvβ1C (carboxyl terminal 329 amino acids of the Kvα1 subfamily), Kvp2 (amino acids 1–367); Kv1.1-N terminus (amino acids 1–168), Kv1.2 N-terminus (amino acids 1–124), Kv1.4 N-terminus (amino acids 1–305), Kv1.4 C-terminus (amino acids 562–654), Kv1.5 N-terminus (amino acids 1–248), Kv2.1 N-terminus (amino acids 1–168), Kv2.2 N-terminus (amino acids 1–185), Kv6.1 N-terminus (amino acids 1–209), Kir2.2 N-terminus (amino acids 1–86), and HERG N-terminus (amino acids 1–396). The ability of human Gu-binding protein (GBP) to bind to these fragments was also determined.

Protein-protein interactions were tested by co-transformation of the yeast host strain Y190 with a pGAD10 plasmid containing inserts encoding KChAP-Y, KChAP or GBP with a pGBT9 plasmid containing an insert encoding one of the K+ channel protein fragments. pGBT9 is a GAL4 DNA binding domain [BD] vector. Co-transformants were plated on medium lacking trp and leu and grown for 2.5 days at 30° C. Yeast colonies were lifted to paper filters and assayed for β-galactosidase activity. Appearance of blue color within 8 hours was scored as a positive interaction between the proteins encoded by the two plasmids.

KChAP and KChAP-Y interacted with the fragments in a similar manner. KChAP interacted with the N-terminus of Kvα1 subunits and the Kvα2 subunits. KChAP also associated with the C terminus of Kvβ1 and Kvβ2 with no apparent interaction with the Kvβ1.2 N-terminus. No binding was observed to the C-terminus of Kv1.4, nor to the N-termini of either HERG, Kir2.2, or Kv6.1. KChAP-Y interacted with the N-termini of Kv1.1, Kv1.2, Kv1.4, and Kv1.5. No interaction was evident between the Kv1.4 C-terminus and KChAP-Y. KChAP-Y also interacted with the N-termini of Kv2.1 and Kv2.2, but not with the N-terminus of the electrically silent Kv2 partner, Kv6.1 Further specificity for a subset of Kv channels was apparent from the lack of interaction with the N-terminus of the inward rectifier K+ channel, Kir2.2, and the N-terrninus of the delayed rectifier K+channel, HERG. Thus, KChAP-Y both interact with the C-terminus of Kvα subunits as well as the N-termini of Kv1 and Kv2 α-subunits.

The minimal KChAP sequence sufficient for Kvα and Kvβ binding was determined by expressing fragments of KChAP in yeast two-hybrid assays with the Kv fragments. The results indicated that the Kvα and Kv, binding domain of KChAP is localized to a region between amino acids W310 and L407. Gu binding protein did not interact with any of the fragments. Thus, although KChAP shares 50% homology with GBP, interaction with Kvβ and Kvα subunits appears to be a unique feature of KChAP.

(b) Direct Procedure for Monitoring Interaction of KChAP and Kvα and Kvβ subunits The direct procedure involved immunoprecipitation of protein complexes produced by in vitro translation of cRNA for c-myc-KChAP and cRNA for the α-subunit Kv2. 1. These cRNA molecules were translated in vitro either separately to produce individual proteins or together to produce complexes in rabbit reticulocyte lysates in the presence of $^{35}$S-methionine using the Retic Lysate IVT kit (Ambion). For immunoprecipitation (IP), 10 μl aliquots of each translation mixture were diluted into 1 ml IP buffer (1% Triton X-100, 150 mM NaCl, 50 mM Tris pH 7.5, 1 mM EDTA). To monitor the ability of the two proteins to associate after translation, 10 μl aliquots of individual translates of Kv2.1 and c-myc-KChAP were mixed in 1 ml IP buffer prior to addition of antibody. IP was performed with two primary antibodies: anti-Kv2.1 polyclonal (1:100 dilution; Upstate Biotechnology, Inc.) or anti-c-myc monoclonal (1:400; Boehringer Mannheim). After addition of the primary antibody, the reactions were mixed gently overnight at 4° C. Immune complexes were collected on magnetic beads coupled to either anti-rabbit or anti- mouse secondary antibodies (Dynal, Inc.). After four washes in IP buffer, bound protein was eluted by boiling in SDS sample buffer, and analyzed on 10% polyacrylamide/SDS gels. The gel was fixed, soaked in Amplify (Amersham), and radiolabeled protein detected by fluorography.

The anti-Kv2.1 antibody immuno-precipitated complexes of Kv2.1 and c-myc-KChAP from translation reactions in which the two proteins were co-translated. The formation of a complex between KChAP and Kv2. 1 shows a direct interaction between the two proteins . No complexes of Kv2.1 and c-myc-KChAP were detected in samples in which the Kv2.1 and c-myc-KchAP were translated separately and mixed together before the addition of primary antibody This result suggests that the association of KChAP with Kv2.1 occurs co-translationally since the mature proteins added after translation did not co-immunoprecipitate.

Altering the Effect of Kvβ1-C on Kv1.5 Currents

Xenopus oocytes were co-injected with cRNA molecules encoding KChAP and cRNA molecules encoding Kv1.5 a subunit and Kvβ1-C. Kvβ1-C is known to interact with the Kv1.5 a subunit within the cell and to decrease Kv1.5 currents. As a control, Xenopus oocytes were injected with cRNA encoding the Kv1.5 α subunit alone or with cRNA molecules encoding Kv1.5 a subunit and Kvβ1-C. Whole cell-currents were measured five days after injection. Holding potential was –80 mV and pulses were from –70 mV to +70 mV in 10 mV steps with 5 mM K+ in the bath solution.

Co-injection into cells of cRNA encoding KChAP and cRNA's encoding Kv1.5 a subunit and Kvβ1-C blocked the effect of Kvβ1-C on Kv1.5 currents.

Presence of KChAP in the Nucleus

Examination of the COS-7 cells and mouse L cells transfected with c-myc-KChAP cDNA and stained with FITC-labeled c-myc antibodies indicate that at least a portion of KChAP is located in the nucleus.

KChAP Expression in Rat Tissues

A $^{32}$P-labeled riboprobe was prepared from a fragment of rat KChAP cDNA encoding the C-terminal 167 amino acids. This is the region of the KChAP protein which differs most from GBP. The riboprobe was used to probe A rat Multiple Tissue Northern blot (2µg poly A$^+$ RNA per lane) from Clontech. The hybridization was done overnight in NorthemMax hybridization buffer from Ambion at 68° C. The blot was washed with in 0.1×SSC/0.1% SDS at 70° C. Autoradiography was performed for 5 hours at –70° C. with Kodak Biomax MS film and intensifying screen. The results indicated that KChAP transcripts are most abundant in heart, brain, skeletal muscle, lung, spleen and kidney.

Interaction of KChAP with the Tumor Suppresser Product p53

The interaction of KChAP with the tumor suppresser gene product p53 was examined using the yeast two-hybrid system. The results indicated that p53 binds to the Kvα/Kvβ binding domain of KChAP. Co-injection into Xenopus oocytes of cRNA molecules that encode p53 along with cRNA molecules that encode KCHAP and the Kv2.1 α subunit suppressed the stimulatory effect of KChAP on formation of Kv2.1 channels.

Testing the Effects of a Compound on Current Flow through Kv Channels

In order to test the stimulatory or inhibitory effect of a compound, particularly a pharmacological agent, on the flow of current through Kv channels, it is desirable to have a model system comprising a population of cells that have increased numbers of Kv channels on their cellular plasma membranes. Such model system is especially suitable for measuring small changes in current flow. Such model systems are prepared by co-injecting into host cells cRNA. molecules encoding KChAP and cRNA molecules encoding a Kvα subunit. The encoding regions for KChAP and for the Kvα subunit may both be on a single cRNA molecule, or the encoding regions for KCHAP and for the Kvα subunit may be on separate cRNA molecules. Preferably, the Kvα subunit is an exogenous Kvα subunit, i.e., the Kvα subunit is not normally expressed in the cell. Such model systems are especially useful for monitoring the effect of a compound on a particular Kv channel, i.e., the Kv channel formed by assembly of a plurality of the exogenous Kvα subunits. Thereafter, the cells are cultured for a time and under conditions which permit transformation of the host cells, i.e., expression of the co-injected cRNA molecules and assembly of Kv channels comprising the corresponding Kvα subunits.

The compound, which has been dissolved in a suitable carrier, is added to the culture medium of a test population of transformed host cells. Preferably, a plurality of concentrations of the compound are added to a corresponding plurality of test populations. The compound is also added to the culture medium of a control population of cells that have not been tranformed, i.e., cRNA molecules encoding KChaP and the Kvα subunit are not injected into the cells. Thereafter, whole cell currents are measured using conventional techniques, such as for example, using a two microelectrode voltage-clamp technique and the gigaseal patch clamp technique. A difference between whole cell currents in the control population and the test populations is indicative of a stimulatory or inhibitory effect of the compound on the Kv channels formed by the exogenous Kvα subunit. Such measurements are also used to determine the effective compound dosage.

While the invention has been described to some degree of particularity, various adaptations and modifications can be made without departing from the scope of the invention as defined in the appended claims.

What is claimed is:

1. An isolated polynucleotide comprising a nucleotide sequence encoding a KChAP protein which binds to Kvα subunits and increases number of Kv channels in transfected cell or a nucleotide sequence complementary to a nucleotide sequence encoding said KChAP protein, wherein said KChAP protein comprises an amino acid sequence which is at least 95% identical to SEQ ID NO: 2 or SEQ ID NO: 4.

2. The polynucleotide of claim 1 wherein said sequence encodes a protein selected from the group consisting of a human KChAP protein comprising an amino acid sequence which is at least 95% identical to SEQ ID NO: 4 and a rat KChAP protein comprising an amino acid sequence which is at-least 95% identical to SEQ ID NO:2.

3. An isolated polynucleotide comprising a nucleotide sequence encoding a protein selected from the group consisting of a rat KChAP protein which binds to Kvα subunits and increases number of Kv channels in transfected cell comprising an amino acid sequence which is at least 95% identical to SEQ ID NO:2, a human KChAP protein which binds to Kvα subunits and increases number of Kv channels in transfected cell comprising an amino acid sequence which at least 95% identical to SEQ ID NO: 4; and a variant of said rat and said human KChAP proteins, said variant comprising the amino acid sequence of SEQ ID NO: 6.

4. The polynucleotide of claim 1 wherein said nucleotide sequence encodes a KChAP protein comprising an amino acid sequence selected from the group consisting of:

(a) the amino acid sequence of SEQ ID NO: 2;

(b) the amino acid sequence of SEQ ID NO: 4; and (c) the amino acid sequence of SEQ ID NO: 6.

5. The polynucleotide of claim 3 wherein the nucleotide sequence encodes a rat KChAP protein comprising the amino acid sequence of SEQ ID NO: 2or an allelic variant thereof.

6. The polynucleotide of claim 3 wherein the nucleotide sequence encodes a human KCHAP protein comprising the amino acid sequence of SEQ ID NO: 4, or an allelic variant thereof.

7. The polynucleotide of claim 1 wherein said polynucleotide comprises a nucleotide sequence selected from the group consisting of:

a) a sequence which is at least 95% identical to the nucleotide sequence of SEQ ID NO:1;

b) a sequence complementary to the nucleotide sequence of SEQ ID NO: 1;

c) a sequence which is at least 95% identical to the nucleotide sequence of SEQ ID NO:3; and d) a sequence complementary to the nucleotide sequence of SEQ ID NO: 3.

8. The polynucleotide of claim 1 wherein said KCHAP protein binds to the N-termini of the Kvα subunits Kv2.1, Kv2.2, Kv1.3, and Kv4.3 and to the C-terminus of Kvβ1.2 and wherein said KChAP protein comprises a Kvα/Kvβ binding domain which comprises the amino acid sequence of SEQ ID NO: 10.

9. The polynucleotide of claim 8 wherein said protein further comprises a C terminal domain which comprises the amino acid sequence of SEQ ID NO: 11.

10. A host cell comprising a polynucleotide encoding a KChAP protein, which binds to Kvα subunits and increases number of Kv channels in transfected cell said KChAP protein comprising an amino acid sequence which is at least 95% identical to SEO ID NO: 4 or SEO ID. NO:2, and a polynucleotide encoding an exogenous Kvα subunit.

11. The host cell of claim 10 wherein the Kvα subunit is selected from the group consisting of Kv2.1, Kv2.2, Kv1.3 and Kv4.3.

12. A host cell comprising an expression vector comprising a nucleic acid sequence which encodes a rat KChAP protein which binds to Kvα subunits and increases number of Kv channels in transfected cell, wherein said protein comprises an amino acid sequence which is at least 95% identical to the amino acid sequence of SEQ ID NO:2 or the amino acid sequence of SEQ ID NO:4.

13. The polynucleotide of claim 7 wherein the polynucleotide comprises the sequence of SEQ ID NO: 1 or the sequence of SEQ ID NO:3.

* * * * *

UNITED STATES PATENT AND TRADEMARK OFFICE
CERTIFICATE OF CORRECTION

PATENT NO.   : 6,207,422 B1
DATED        : March 27, 2001
INVENTOR(S)  : Arthur M. Brown, Barbara A. Wible and Qing Yang It is certified that error appears in the above-identified patent and that said Letters Patent is hereby corrected as shown below:

<u>Column 1,</u>
Line 6, before "BACKGROUND OF THE INVENTION" please insert
-- This invention was made in part with government support under grans HL-57416, HL-55404, HL-36930, and NS-23877 from the National Institutes of Health. The government has certain rights in the invention. --

Signed and Sealed this

Eighteenth Day of February, 2003

JAMES E. ROGAN
*Director of the United States Patent and Trademark Office*

SEQUENCE LISTING (1) GENERAL INFORMATION:

(iii) NUMBER OF SEQUENCES: 13

(2) INFORMATION FOR SEQ ID NO:1:

(i) SEQUENCE CHARACTERISTICS:
      (A) LENGTH: 1725 base pairs
      (B) TYPE: nucleic acid
      (C) STRANDEDNESS: both
      (D) TOPOLOGY: linear -continued (ii) MOLECULE TYPE: cDNA (iii) HYPOTHETICAL: NO (iv) ANTI-SENSE: NO (ix) FEATURE:
    (A) NAME/KEY: CDS
    (B) LOCATION: 1..1725

(xi) SEQUENCE DESCRIPTION: SEQ ID NO:1:

```
ATG AAG ATC AAA GAA CTT TAC CGC AGG CGC TTT CCC CGG AAG ACC CTG      48
Met Lys Ile Lys Glu Leu Tyr Arg Arg Arg Phe Pro Arg Lys Thr Leu
 1               5                  10                  15

GGG CCT TCC GAT CTC TCT TTG CTC TCT TTG CCC CCT GGC ACC TCT CCT      96
Gly Pro Ser Asp Leu Ser Leu Leu Ser Leu Pro Pro Gly Thr Ser Pro
             20                  25                  30

GTA GGC TCC CCC AGC CCC CTT GCT TCC ATT CCT CCC ACC CTC CTG ACC     144
Val Gly Ser Pro Ser Pro Leu Ala Ser Ile Pro Pro Thr Leu Leu Thr
         35                  40                  45

CCT GGC ACC TTG CTG GGC CCT AAG CGT GAG GTG GAC ATG CAC CCT CCT     192
Pro Gly Thr Leu Leu Gly Pro Lys Arg Glu Val Asp Met His Pro Pro
     50                  55                  60

CTG CCC CAG CCT GTG CAC CCT GAC GTC ACC ATG AAA CCA CTG CCC TTC     240
Leu Pro Gln Pro Val His Pro Asp Val Thr Met Lys Pro Leu Pro Phe
 65                  70                  75                  80

TAC GAA GTC TAC GGA GAG CTC ATC CGG CCG ACC ACC CTT GCG TCC ACC     288
Tyr Glu Val Tyr Gly Glu Leu Ile Arg Pro Thr Thr Leu Ala Ser Thr
                 85                  90                  95

TCC AGT CAG AGG TTT GAG GAA GCC CAC TTT ACC TTT GCA CTC ACT CCC     336
Ser Ser Gln Arg Phe Glu Glu Ala His Phe Thr Phe Ala Leu Thr Pro
            100                 105                 110

CAG CAG CTG CAG CAG ATT CTC ACA TCC AGG GAG GTT CTG CCA GGA GCC     384
Gln Gln Leu Gln Gln Ile Leu Thr Ser Arg Glu Val Leu Pro Gly Ala
        115                 120                 125

AAG TGC GAT TAT ACC ATA CAA GTG CAG CTC AGG TTC TGT CTC TGT GAG     432
Lys Cys Asp Tyr Thr Ile Gln Val Gln Leu Arg Phe Cys Leu Cys Glu
    130                 135                 140

ACC AGC TGC CCC CAG GAG GAC TAT TTC CCC CCT AAC CTC TTT GTC AAG     480
Thr Ser Cys Pro Gln Glu Asp Tyr Phe Pro Pro Asn Leu Phe Val Lys
145                 150                 155                 160

GTT AAT GGG AAA CTC TGC CCC CTG CCG GGT TAC CTC CCT CCA ACC AAG     528
Val Asn Gly Lys Leu Cys Pro Leu Pro Gly Tyr Leu Pro Pro Thr Lys
                165                 170                 175

AAT GGA GCT GAG CCC AAG AGG CCT AGT CGT CCA ATC AAC ATC ACA CCC     576
Asn Gly Ala Glu Pro Lys Arg Pro Ser Arg Pro Ile Asn Ile Thr Pro
            180                 185                 190

CTG GCT CGT CTC TCA GCC ACT GTT CCC AAC ACC ATA GTG GTT AAC TGG     624
Leu Ala Arg Leu Ser Ala Thr Val Pro Asn Thr Ile Val Val Asn Trp
        195                 200                 205

TCA TCT GAG TTT GGA CGG AAT TAC TCC TTG TCT GTG TAC CTG GTG AGG     672
Ser Ser Glu Phe Gly Arg Asn Tyr Ser Leu Ser Val Tyr Leu Val Arg
    210                 215                 220

CAG TTG ACT GCA GGG ACC CTG CTA CAA AAG CTC AGA GCC AAG GGT ATC     720
Gln Leu Thr Ala Gly Thr Leu Leu Gln Lys Leu Arg Ala Lys Gly Ile
225                 230                 235                 240

CGG AAT CCA GAC CAT TCC CGA GCA CTG ATC AAG GAG AAA TTG ACT GCT     768
Arg Asn Pro Asp His Ser Arg Ala Leu Ile Lys Glu Lys Leu Thr Ala
                245                 250                 255

GAC CCC GAC AGT GAA GTG GCT ACT ACA AGT CTC CGG GTG TCA CTC ATG     816
Asp Pro Asp Ser Glu Val Ala Thr Thr Ser Leu Arg Val Ser Leu Met
            260                 265                 270
```

```
TGC CCG CTG GGG AAG ATG CGC CTG ACT GTC CCA TGC CGC GCT CTC ACC     864
Cys Pro Leu Gly Lys Met Arg Leu Thr Val Pro Cys Arg Ala Leu Thr
            275                 280                 285

TGT GCC CAC CTG CAG AGT TTC GAT GCT GCC CTT TAT CTA CAG ATG AAT     912
Cys Ala His Leu Gln Ser Phe Asp Ala Ala Leu Tyr Leu Gln Met Asn
    290                 295                 300

GAG AAA AAG CCA ACA TGG ACG TGC CCT GTG TGT GAC AAG AAG GCT CCC     960
Glu Lys Lys Pro Thr Trp Thr Cys Pro Val Cys Asp Lys Lys Ala Pro
305                 310                 315                 320

TAT GAG TCA CTG ATT ATT GAT GGT TTA TTC ATG GAA ATT CTT AAT TCC    1008
Tyr Glu Ser Leu Ile Ile Asp Gly Leu Phe Met Glu Ile Leu Asn Ser
                325                 330                 335

TGT TCG GAT TGT GAT GAG ATC CAG TTC ATG GAA GAT GGA TCC TGG TGT    1056
Cys Ser Asp Cys Asp Glu Ile Gln Phe Met Glu Asp Gly Ser Trp Cys
            340                 345                 350

CCA ATG AAA CCC AAG AAG GAG GCA TCC GAG GTT TGC CCC CCA CCA GGG    1104
Pro Met Lys Pro Lys Lys Glu Ala Ser Glu Val Cys Pro Pro Pro Gly
        355                 360                 365

TAT GGG CTG GAT GGT CTC CAG TAT AGC CCA GTC CAG GAG GGA AAT CAG    1152
Tyr Gly Leu Asp Gly Leu Gln Tyr Ser Pro Val Gln Glu Gly Asn Gln
    370                 375                 380

TCA GAG AAT AAG AAG AGG GTT GAA GTC ATT GAC TTG ACA ATC GAA AGC    1200
Ser Glu Asn Lys Lys Arg Val Glu Val Ile Asp Leu Thr Ile Glu Ser
385                 390                 395                 400

TCA TCA GAT GAG GAA GAT CTG CCC CCC ACC AAG AAG CAC TGC CCT GTT    1248
Ser Ser Asp Glu Glu Asp Leu Pro Pro Thr Lys Lys His Cys Pro Val
                405                 410                 415

ACC TCG GCT GCC ATT CCA GCC CTT CCT GGA AGC AAA GGA GCC CTG ACC    1296
Thr Ser Ala Ala Ile Pro Ala Leu Pro Gly Ser Lys Gly Ala Leu Thr
            420                 425                 430

TCT GGT CAC CAG CCG TCT TCG GTG CTG CGG AGC CCT GCA ATG GGT ACA    1344
Ser Gly His Gln Pro Ser Ser Val Leu Arg Ser Pro Ala Met Gly Thr
        435                 440                 445

CTG GGC AGT GAT TTC CTG TCT AGT CTC CCA CTA CAT GAG TAC CCA CCT    1392
Leu Gly Ser Asp Phe Leu Ser Ser Leu Pro Leu His Glu Tyr Pro Pro
    450                 455                 460

GCC TTC CCG CTG GGG GCT GAC ATC CAA GGT TTA GAT TTA TTT TCT TTC    1440
Ala Phe Pro Leu Gly Ala Asp Ile Gln Gly Leu Asp Leu Phe Ser Phe
465                 470                 475                 480

CTT CAG ACT GAG AGT CAG CAC TAC AGC CCT TCA GTT ATC ACT TCA CTA    1488
Leu Gln Thr Glu Ser Gln His Tyr Ser Pro Ser Val Ile Thr Ser Leu
                485                 490                 495

GAT GAG CAG GAC ACC CTT GGC CAC TTC TTC CAA TTC CGG GGA ACC CCT    1536
Asp Glu Gln Asp Thr Leu Gly His Phe Phe Gln Phe Arg Gly Thr Pro
            500                 505                 510

CCC CAC TTC CTG GGC CCA CTG GCC CCC ACA TTG GGG AGC TCT CAC CGC    1584
Pro His Phe Leu Gly Pro Leu Ala Pro Thr Leu Gly Ser Ser His Arg
        515                 520                 525

AGC GCC ACT CCA GCA CCC GCT CCT GGC CGT GTC AGC AGC ATT GTG GCT    1632
Ser Ala Thr Pro Ala Pro Ala Pro Gly Arg Val Ser Ser Ile Val Ala
    530                 535                 540

CCT GGG AGT TCC TTG AGG GAA GGG CAT GGA GGA CCC CTG CCT TCC GGT    1680
Pro Gly Ser Ser Leu Arg Glu Gly His Gly Gly Pro Leu Pro Ser Gly
545                 550                 555                 560

CCC TCT TTG ACT GGC TGT CGG TCA GAC GTC ATT TCC TTG GAC TGA        1725
Pro Ser Leu Thr Gly Cys Arg Ser Asp Val Ile Ser Leu Asp  *
                565                 570                 575
```

-continued (2) INFORMATION FOR SEQ ID NO:2:

(i) SEQUENCE CHARACTERISTICS:
        (A) LENGTH: 574 amino acids
        (B) TYPE: amino acid
        (D) TOPOLOGY: linear (ii) MOLECULE TYPE: protein (xi) SEQUENCE DESCRIPTION: SEQ ID NO:2:

```
Met Lys Ile Lys Glu Leu Tyr Arg Arg Arg Phe Pro Arg Lys Thr Leu
 1               5                  10                  15

Gly Pro Ser Asp Leu Ser Leu Leu Ser Leu Pro Pro Gly Thr Ser Pro
            20                  25                  30

Val Gly Ser Pro Ser Pro Leu Ala Ser Ile Pro Pro Thr Leu Leu Thr
        35                  40                  45

Pro Gly Thr Leu Leu Gly Pro Lys Arg Glu Val Asp Met His Pro Pro
    50                  55                  60

Leu Pro Gln Pro Val His Pro Asp Val Thr Met Lys Pro Leu Pro Phe
65                  70                  75                  80

Tyr Glu Val Tyr Gly Glu Leu Ile Arg Pro Thr Thr Leu Ala Ser Thr
                85                  90                  95

Ser Ser Gln Arg Phe Glu Glu Ala His Phe Thr Phe Ala Leu Thr Pro
            100                 105                 110

Gln Gln Leu Gln Gln Ile Leu Thr Ser Arg Glu Val Leu Pro Gly Ala
        115                 120                 125

Lys Cys Asp Tyr Thr Ile Gln Val Gln Leu Arg Phe Cys Leu Cys Glu
    130                 135                 140

Thr Ser Cys Pro Gln Glu Asp Tyr Phe Pro Pro Asn Leu Phe Val Lys
145                 150                 155                 160

Val Asn Gly Lys Leu Cys Pro Leu Pro Gly Tyr Leu Pro Pro Thr Lys
                165                 170                 175

Asn Gly Ala Glu Pro Lys Arg Pro Ser Arg Pro Ile Asn Ile Thr Pro
            180                 185                 190

Leu Ala Arg Leu Ser Ala Thr Val Pro Asn Thr Ile Val Val Asn Trp
        195                 200                 205

Ser Ser Glu Phe Gly Arg Asn Tyr Ser Leu Ser Val Tyr Leu Val Arg
    210                 215                 220

Gln Leu Thr Ala Gly Thr Leu Leu Gln Lys Leu Arg Ala Lys Gly Ile
225                 230                 235                 240

Arg Asn Pro Asp His Ser Arg Ala Leu Ile Lys Glu Lys Leu Thr Ala
                245                 250                 255

Asp Pro Asp Ser Glu Val Ala Thr Thr Ser Leu Arg Val Ser Leu Met
            260                 265                 270

Cys Pro Leu Gly Lys Met Arg Leu Thr Val Pro Cys Arg Ala Leu Thr
        275                 280                 285

Cys Ala His Leu Gln Ser Phe Asp Ala Ala Leu Tyr Leu Gln Met Asn
    290                 295                 300

Glu Lys Lys Pro Thr Trp Thr Cys Pro Val Cys Asp Lys Lys Ala Pro
305                 310                 315                 320

Tyr Glu Ser Leu Ile Ile Asp Gly Leu Phe Met Glu Ile Leu Asn Ser
                325                 330                 335

Cys Ser Asp Cys Asp Glu Ile Gln Phe Met Glu Asp Gly Ser Trp Cys
            340                 345                 350

Pro Met Lys Pro Lys Lys Glu Ala Ser Glu Val Cys Pro Pro Pro Gly
        355                 360                 365
```

-continued

```
Tyr Gly Leu Asp Gly Leu Gln Tyr Ser Pro Val Gln Glu Gly Asn Gln
    370                 375                 380

Ser Glu Asn Lys Lys Arg Val Glu Val Ile Asp Leu Thr Ile Glu Ser
385                 390                 395                 400

Ser Ser Asp Glu Glu Asp Leu Pro Pro Thr Lys Lys His Cys Pro Val
                405                 410                 415

Thr Ser Ala Ala Ile Pro Ala Leu Pro Gly Ser Lys Gly Ala Leu Thr
            420                 425                 430

Ser Gly His Gln Pro Ser Ser Val Leu Arg Ser Pro Ala Met Gly Thr
        435                 440                 445

Leu Gly Ser Asp Phe Leu Ser Ser Leu Pro Leu His Glu Tyr Pro Pro
    450                 455                 460

Ala Phe Pro Leu Gly Ala Asp Ile Gln Gly Leu Asp Leu Phe Ser Phe
465                 470                 475                 480

Leu Gln Thr Glu Ser Gln His Tyr Ser Pro Ser Val Ile Thr Ser Leu
                485                 490                 495

Asp Glu Gln Asp Thr Leu Gly His Phe Phe Gln Phe Arg Gly Thr Pro
                500                 505                 510

Pro His Phe Leu Gly Pro Leu Ala Pro Thr Leu Gly Ser Ser His Arg
            515                 520                 525

Ser Ala Thr Pro Ala Pro Ala Pro Gly Arg Val Ser Ser Ile Val Ala
        530                 535                 540

Pro Gly Ser Ser Leu Arg Glu Gly His Gly Gly Pro Leu Pro Ser Gly
545                 550                 555                 560

Pro Ser Leu Thr Gly Cys Arg Ser Asp Val Ile Ser Leu Asp
                565                 570                 575
```

(2) INFORMATION FOR SEQ ID NO:3:

(i) SEQUENCE CHARACTERISTICS:
        (A) LENGTH: 1725 base pairs
        (B) TYPE: nucleic acid
        (C) STRANDEDNESS: both
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: CDS
        (B) LOCATION: 1..1725

(xi) SEQUENCE DESCRIPTION: SEQ ID NO:3:

```
ATG AAG ATC AAA GAG CTT TAC CGA CGA CGC TTT CCC CGG AAG ACC CTG      48
Met Lys Ile Lys Glu Leu Tyr Arg Arg Arg Phe Pro Arg Lys Thr Leu
 1               5                  10                  15

GGG CCC TCT GAT CTC TCC CTT CTC TCT TTG CCC CCT GGC ACC TCT CCT      96
Gly Pro Ser Asp Leu Ser Leu Leu Ser Leu Pro Pro Gly Thr Ser Pro
            20                  25                  30

GTA GGC TCC CCT GGT CCT CTA GCT CCC ATT CCC CCA ACG CTG TTG GCC     144
Val Gly Ser Pro Gly Pro Leu Ala Pro Ile Pro Pro Thr Leu Leu Ala
        35                  40                  45

CCT GGC ACC CTG CTG GGC CCC AAG CGT GAG GTG GAC ATG CAC CCC CCT     192
Pro Gly Thr Leu Leu Gly Pro Lys Arg Glu Val Asp Met His Pro Pro
    50                  55                  60

CTG CCC CAG CCT GTG CAC CCT GAT GTC ACC ATG AAA CCA TTG CCC TTC     240
Leu Pro Gln Pro Val His Pro Asp Val Thr Met Lys Pro Leu Pro Phe
65                  70                  75                  80
```

```
TAT GAA GTC TAT GGG GAG CTC ATC CGG CCC ACC ACC CTT GCA TCC ACT          288
Tyr Glu Val Tyr Gly Glu Leu Ile Arg Pro Thr Thr Leu Ala Ser Thr
                 85                  90                  95

TCT AGC CAG CGG TTT GAG GAA GCG CAC TTT ACC TTT GCC CTC ACA CCC          336
Ser Ser Gln Arg Phe Glu Glu Ala His Phe Thr Phe Ala Leu Thr Pro
                100                 105                 110

CAG CAA GTG CAG CAG ATT CTT ACA TCC AGA GAG GTT CTG CCA GGA GCC          384
Gln Gln Val Gln Gln Ile Leu Thr Ser Arg Glu Val Leu Pro Gly Ala
                115                 120                 125

AAA TGT GAT TAT ACC ATA CAG GTG CAG CTA AGG TTC TGT CTC TGT GAG          432
Lys Cys Asp Tyr Thr Ile Gln Val Gln Leu Arg Phe Cys Leu Cys Glu
130                 135                 140

ACC AGC TGC CCC CAG GAA GAT TAT TTT CCC CCC AAC CTC TTT GTC AAG          480
Thr Ser Cys Pro Gln Glu Asp Tyr Phe Pro Pro Asn Leu Phe Val Lys
145                 150                 155                 160

GTT AAT GGG AAA CTG TGC CCC CTG CCG GGT TAC CTT CCC CCA ACC AAG          528
Val Asn Gly Lys Leu Cys Pro Leu Pro Gly Tyr Leu Pro Pro Thr Lys
                165                 170                 175

AAT GGG GCC GAG CCC AAG AGG CCC AGC CGC CCC ATC AAC ATC ACA CCC          576
Asn Gly Ala Glu Pro Lys Arg Pro Ser Arg Pro Ile Asn Ile Thr Pro
                180                 185                 190

CTG GCT CGA CTC TCA GCC ACT GTT CCC AAC ACC ATT GTG GTC AAT TGG          624
Leu Ala Arg Leu Ser Ala Thr Val Pro Asn Thr Ile Val Val Asn Trp
                195                 200                 205

TCA TCT GAG TTC GGA CGG AAT TAC TCC TTG TCT GTG TAC CTG GTG AGG          672
Ser Ser Glu Phe Gly Arg Asn Tyr Ser Leu Ser Val Tyr Leu Val Arg
210                 215                 220

CAG TTG ACT GCA GGA ACC CTT CTA CAA AAA CTC AGA GCA AAG GGT ATC          720
Gln Leu Thr Ala Gly Thr Leu Leu Gln Lys Leu Arg Ala Lys Gly Ile
225                 230                 235                 240

CGG AAC CCA GAC CAC TCG CGG GCA CTG ATC AAG GAG AAA TTG ACT GCT          768
Arg Asn Pro Asp His Ser Arg Ala Leu Ile Lys Glu Lys Leu Thr Ala
                245                 250                 255

GAC CCT GAC AGT GAG GTG GCC ACT ACA AGT CTC CGG GTG TCA CTC ATG          816
Asp Pro Asp Ser Glu Val Ala Thr Thr Ser Leu Arg Val Ser Leu Met
                260                 265                 270

TGC CCG CTA GGG AAG ATG CGC CTG ACT GTC CCT TGT CGT GCC CTC ACC          864
Cys Pro Leu Gly Lys Met Arg Leu Thr Val Pro Cys Arg Ala Leu Thr
                275                 280                 285

TGT GCC CAC CTG CAG AGC TTC GAT GCT GCC CTT TAT CTA CAG ATG AAT          912
Cys Ala His Leu Gln Ser Phe Asp Ala Ala Leu Tyr Leu Gln Met Asn
                290                 295                 300

GAG AAG AAG CCT ACA TGG ACA TGT CCT GTG TGT GAC AAG AAG GCT CCC          960
Glu Lys Lys Pro Thr Trp Thr Cys Pro Val Cys Asp Lys Lys Ala Pro
305                 310                 315                 320

TAT GAA TCT CTT ATC ATT GAT GGT TTA TTT ATG GAG ATT CTT AGT TCC         1008
Tyr Glu Ser Leu Ile Ile Asp Gly Leu Phe Met Glu Ile Leu Ser Ser
                325                 330                 335

TGT TCA GAT TGT GAT GAG ATC CAA TTC ATG GAA GAT GGA TCC TGG TGC         1056
Cys Ser Asp Cys Asp Glu Ile Gln Phe Met Glu Asp Gly Ser Trp Cys
                340                 345                 350

CCA ATG AAA CCC AAG AAG GAG GCA TCT GAG GTT TGC CCC CCG CCA GGG         1104
Pro Met Lys Pro Lys Lys Glu Ala Ser Glu Val Cys Pro Pro Pro Gly
            355                 360                 365

TAT GGG CTG GAT GGC CTC CAG TAC AGC CCA GTC CAG GGG GGA GAT CCA         1152
Tyr Gly Leu Asp Gly Leu Gln Tyr Ser Pro Val Gln Gly Gly Asp Pro
            370                 375                 380

TCA GAG AAT AAG AAG AAG GTC GAA GTT ATT GAC TTG ACA ATA GAA AGC         1200
Ser Glu Asn Lys Lys Lys Val Glu Val Ile Asp Leu Thr Ile Glu Ser
385                 390                 395                 400
```

-continued

```
TCA TCA GAT GAG GAG GAT CTG CCC CCT ACC AAG AAG CAC TGT TCT GTC      1248
Ser Ser Asp Glu Glu Asp Leu Pro Pro Thr Lys Lys His Cys Ser Val
            405                 410                 415

ACC TCA GCT GCC ATC CCG GCC CTA CCT GGA AGC AAA GGA GTC CTG ACA      1296
Thr Ser Ala Ala Ile Pro Ala Leu Pro Gly Ser Lys Gly Val Leu Thr
                420                 425                 430

TCT GGC CAC CAG CCA TCC TCG GTG CTA AGG AGC CCT GCT ATG GGC ACG      1344
Ser Gly His Gln Pro Ser Ser Val Leu Arg Ser Pro Ala Met Gly Thr
                    435                 440                 445

TTG GGT GGG GAT TTC CTG TCC AGT CTC CCA CTA CAT GAG TAC CCA CCT      1392
Leu Gly Gly Asp Phe Leu Ser Ser Leu Pro Leu His Glu Tyr Pro Pro
        450                 455                 460

GCC TTC CCA CTG GGA GCC GAC ATC CAA GGT TTA GAT TTA TTT TCA TTT      1440
Ala Phe Pro Leu Gly Ala Asp Ile Gln Gly Leu Asp Leu Phe Ser Phe
465                 470                 475                 480

CTT CAG ACA GAG AGT CAG CAC TAT GGC CCC TCT GTC ATC ACC TCA CTA      1488
Leu Gln Thr Glu Ser Gln His Tyr Gly Pro Ser Val Ile Thr Ser Leu
                485                 490                 495

GAT GAA CAG GAT GCC CTT GGC CAC TTC TTC CAG TAC CGA GGG ACC CCT      1536
Asp Glu Gln Asp Ala Leu Gly His Phe Phe Gln Tyr Arg Gly Thr Pro
                    500                 505                 510

TCT CAC TTT CTG GGC CCA CTG GCC CCC ACG CTG GGG AGC TCC CAC TGC      1584
Ser His Phe Leu Gly Pro Leu Ala Pro Thr Leu Gly Ser Ser His Cys
        515                 520                 525

AGC GCC ACT CCG GCG CCC CCT CCT GGC CGT GTC AGC AGC ATT GTG GCC      1632
Ser Ala Thr Pro Ala Pro Pro Pro Gly Arg Val Ser Ser Ile Val Ala
530                 535                 540

CCT GGG GGG GCC TTG AGG GAG GGG CAT GGA GGA CCC CTG CCC TCA GGT      1680
Pro Gly Gly Ala Leu Arg Glu Gly His Gly Gly Pro Leu Pro Ser Gly
545                 550                 555                 560

CCC TCT TTG ACT GGC TGT CGG TCA GAC ATC ATT TCC CTG GAC TGA          1725
Pro Ser Leu Thr Gly Cys Arg Ser Asp Ile Ile Ser Leu Asp *
                565                 570                 575
```

(2) INFORMATION FOR SEQ ID NO:4:

(i) SEQUENCE CHARACTERISTICS:
        (A) LENGTH: 574 amino acids
        (B) TYPE: amino acid
        (D) TOPOLOGY: linear (ii) MOLECULE TYPE: protein (xi) SEQUENCE DESCRIPTION: SEQ ID NO:4:

```
Met Lys Ile Lys Glu Leu Tyr Arg Arg Arg Phe Pro Arg Lys Thr Leu
1               5                   10                  15

Gly Pro Ser Asp Leu Ser Leu Leu Ser Leu Pro Pro Gly Thr Ser Pro
            20                  25                  30

Val Gly Ser Pro Gly Pro Leu Ala Pro Ile Pro Pro Thr Leu Leu Ala
        35                  40                  45

Pro Gly Thr Leu Leu Gly Pro Lys Arg Glu Val Asp Met His Pro Pro
    50                  55                  60

Leu Pro Gln Pro Val His Pro Asp Val Thr Met Lys Pro Leu Pro Phe
65                  70                  75                  80

Tyr Glu Val Tyr Gly Glu Leu Ile Arg Pro Thr Thr Leu Ala Ser Thr
                85                  90                  95

Ser Ser Gln Arg Phe Glu Glu Ala His Phe Thr Phe Ala Leu Thr Pro
            100                 105                 110

Gln Gln Val Gln Gln Ile Leu Thr Ser Arg Glu Val Leu Pro Gly Ala
        115                 120                 125
```

-continued

```
Lys Cys Asp Tyr Thr Ile Gln Val Gln Leu Arg Phe Cys Leu Cys Glu
    130                 135                 140
Thr Ser Cys Pro Gln Glu Asp Tyr Phe Pro Asn Leu Phe Val Lys
145                 150                 155                 160
Val Asn Gly Lys Leu Cys Pro Leu Pro Gly Tyr Leu Pro Pro Thr Lys
                165                 170                 175
Asn Gly Ala Glu Pro Lys Arg Pro Ser Arg Pro Ile Asn Ile Thr Pro
            180                 185                 190
Leu Ala Arg Leu Ser Ala Thr Val Pro Asn Thr Ile Val Val Asn Trp
        195                 200                 205
Ser Ser Glu Phe Gly Arg Asn Tyr Ser Leu Ser Val Tyr Leu Val Arg
    210                 215                 220
Gln Leu Thr Ala Gly Thr Leu Leu Gln Lys Leu Arg Ala Lys Gly Ile
225                 230                 235                 240
Arg Asn Pro Asp His Ser Arg Ala Leu Ile Lys Glu Lys Leu Thr Ala
                245                 250                 255
Asp Pro Asp Ser Glu Val Ala Thr Thr Ser Leu Arg Val Ser Leu Met
            260                 265                 270
Cys Pro Leu Gly Lys Met Arg Leu Thr Val Pro Cys Arg Ala Leu Thr
        275                 280                 285
Cys Ala His Leu Gln Ser Phe Asp Ala Ala Leu Tyr Leu Gln Met Asn
    290                 295                 300
Glu Lys Lys Pro Thr Trp Thr Cys Pro Val Cys Asp Lys Lys Ala Pro
305                 310                 315                 320
Tyr Glu Ser Leu Ile Ile Asp Gly Leu Phe Met Glu Ile Leu Ser Ser
                325                 330                 335
Cys Ser Asp Cys Asp Glu Ile Gln Phe Met Glu Asp Gly Ser Trp Cys
            340                 345                 350
Pro Met Lys Pro Lys Lys Glu Ala Ser Glu Val Cys Pro Pro Pro Gly
        355                 360                 365
Tyr Gly Leu Asp Gly Leu Gln Tyr Ser Pro Val Gln Gly Gly Asp Pro
    370                 375                 380
Ser Glu Asn Lys Lys Val Glu Val Ile Asp Leu Thr Ile Glu Ser
385                 390                 395                 400
Ser Ser Asp Glu Glu Asp Leu Pro Pro Thr Lys Lys His Cys Ser Val
                405                 410                 415
Thr Ser Ala Ala Ile Pro Ala Leu Pro Gly Ser Lys Gly Val Leu Thr
            420                 425                 430
Ser Gly His Gln Pro Ser Ser Val Leu Arg Ser Pro Ala Met Gly Thr
        435                 440                 445
Leu Gly Gly Asp Phe Leu Ser Ser Leu Pro Leu His Glu Tyr Pro Pro
    450                 455                 460
Ala Phe Pro Leu Gly Ala Asp Ile Gln Gly Leu Asp Leu Phe Ser Phe
465                 470                 475                 480
Leu Gln Thr Glu Ser Gln His Tyr Gly Pro Ser Val Ile Thr Ser Leu
                485                 490                 495
Asp Glu Gln Asp Ala Leu Gly His Phe Phe Gln Tyr Arg Gly Thr Pro
            500                 505                 510
Ser His Phe Leu Gly Pro Leu Ala Pro Thr Leu Gly Ser Ser His Cys
        515                 520                 525
Ser Ala Thr Pro Ala Pro Pro Gly Arg Val Ser Ser Ile Val Ala
    530                 535                 540
```

```
Pro Gly Gly Ala Leu Arg Glu Gly His Gly Gly Pro Leu Pro Ser Gly
545                 550                 555                 560

Pro Ser Leu Thr Gly Cys Arg Ser Asp Ile Ile Ser Leu Asp
                565                 570                 575
```

(2) INFORMATION FOR SEQ ID NO:5:

(i) SEQUENCE CHARACTERISTICS:
        (A) LENGTH: 99 amino acids
        (B) TYPE: amino acid
        (C) STRANDEDNESS: Not Relevant
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:5:

```
Thr Trp Thr Cys Pro Val Cys Asp Lys Lys Ala Pro Tyr Glu Ser Leu
1               5                   10                  15

Ile Ile Asp Gly Leu Phe Met Glu Ile Leu Ser Ser Cys Ser Asp Cys
                20                  25                  30

Asp Glu Ile Gln Phe Met Glu Asp Gly Ser Trp Cys Pro Met Lys Pro
                35                  40                  45

Lys Lys Glu Ala Ser Glu Val Cys Pro Pro Gly Tyr Gly Leu Asp
50                  55                  60

Gly Leu Gln Tyr Ser Pro Val Gln Gly Gly Asp Pro Ser Glu Asn Lys
65                  70                  75                  80

Lys Lys Val Glu Val Ile Asp Leu Thr Ile Glu Ser Ser Ser Asp Glu
                85                  90                  95

Glu Asp Leu
```

(2) INFORMATION FOR SEQ ID NO:6:

(i) SEQUENCE CHARACTERISTICS:
        (A) LENGTH: 574 amino acids
        (B) TYPE: amino acid
        (C) STRANDEDNESS: Not Relevant
        (D) TOPOLOGY: linear (ii) MOLECULE TYPE: peptide (iii) HYPOTHETICAL: NO (iv) ANTI-SENSE: NO (ix) FEATURE:
        (A) NAME/KEY: Peptide
        (B) LOCATION: 37..38
        (D) OTHER INFORMATION: /note= "glycine or serine"

(ix) FEATURE:
        (A) NAME/KEY: Peptide
        (B) LOCATION: 41..42
        (D) OTHER INFORMATION: /note= "proline or serine"

(ix) FEATURE:
        (A) NAME/KEY: Peptide
        (B) LOCATION: 48..49
        (D) OTHER INFORMATION: /note= "alanine or threonine"

(ix) FEATURE:
        (A) NAME/KEY: Peptide
        (B) LOCATION: 115..116
        (D) OTHER INFORMATION: /note= "valine or leucine"

-continued

```
(ix) FEATURE:
     (A) NAME/KEY: Peptide
     (B) LOCATION: 335..336
     (D) OTHER INFORMATION: /note= "serine or asparagine"

(ix) FEATURE:
     (A) NAME/KEY: Peptide
     (B) LOCATION: 381..382
     (D) OTHER INFORMATION: /note= "glycine or glutamic acid"

(ix) FEATURE:
     (A) NAME/KEY: Peptide
     (B) LOCATION: 383..384
     (D) OTHER INFORMATION: /note= "aspartic acid or
         asparagine"

(ix) FEATURE:
     (A) NAME/KEY: Peptide
     (B) LOCATION: 384..385
     (D) OTHER INFORMATION: /note= "isoproline or glutamine"

(ix) FEATURE:
     (A) NAME/KEY: Peptide
     (B) LOCATION: 390..391
     (D) OTHER INFORMATION: /note= "lysine or arganine"

(ix) FEATURE:
     (A) NAME/KEY: Peptide
     (B) LOCATION: 416..417
     (D) OTHER INFORMATION: /note= "serine or proline"

(ix) FEATURE:
     (A) NAME/KEY: Peptide
     (B) LOCATION: 431..432
     (D) OTHER INFORMATION: /note= "valine or alanine"

(ix) FEATURE:
     (A) NAME/KEY: Peptide
     (B) LOCATION: 451..452
     (D) OTHER INFORMATION: /note= "glycine or serine"

(ix) FEATURE:
     (A) NAME/KEY: Peptide
     (B) LOCATION: 489..490
     (D) OTHER INFORMATION: /note= "glycine or serine"

(ix) FEATURE:
     (A) NAME/KEY: Peptide
     (B) LOCATION: 501..502
     (D) OTHER INFORMATION: /note= "alanine or threonine"

(ix) FEATURE:
     (A) NAME/KEY: Peptide
     (B) LOCATION: 508..509
     (D) OTHER INFORMATION: /note= "tyrosine or phenylalanine"

(ix) FEATURE:
     (A) NAME/KEY: Peptide
     (B) LOCATION: 513..514
     (D) OTHER INFORMATION: /note= "serine or proline"

(ix) FEATURE:
     (A) NAME/KEY: Peptide
     (B) LOCATION: 528..529
     (D) OTHER INFORMATION: /note= "cysteine or arginine"

(ix) FEATURE:
     (A) NAME/KEY: Peptide
     (B) LOCATION: 535..536
     (D) OTHER INFORMATION: /note= "proline or alanine"

(ix) FEATURE:
     (A) NAME/KEY: Peptide
     (B) LOCATION: 547..548
     (D) OTHER INFORMATION: /note= "glycine or serine"
```

(ix) FEATURE:
    (A) NAME/KEY: Peptide
    (B) LOCATION: 548..549
    (D) OTHER INFORMATION: /note= "alanine or serine"

(ix) FEATURE:
    (A) NAME/KEY: Peptide
    (B) LOCATION: 570..571
    (D) OTHER INFORMATION: /note= "isoleucine or valine"

(xi) SEQUENCE DESCRIPTION: SEQ ID NO:6:

```
Met Lys Ile Lys Glu Leu Tyr Arg Arg Phe Pro Arg Lys Thr Leu
1               5                   10                  15

Gly Pro Ser Asp Leu Ser Leu Leu Ser Leu Pro Pro Gly Thr Ser Pro
                20                  25                  30

Val Gly Ser Pro Xaa Pro Leu Ala Xaa Ile Pro Pro Thr Leu Leu Xaa
            35                  40                  45

Pro Gly Thr Leu Leu Gly Pro Lys Arg Glu Val Asp Met His Pro Pro
        50                  55                  60

Leu Pro Gln Pro Val His Pro Asp Val Thr Met Lys Pro Leu Pro Phe
65                  70                  75                  80

Tyr Glu Val Tyr Gly Glu Leu Ile Arg Pro Thr Thr Leu Ala Ser Thr
                85                  90                  95

Ser Ser Gln Arg Phe Glu Glu Ala His Phe Thr Phe Ala Leu Thr Pro
            100                 105                 110

Gln Gln Xaa Gln Gln Ile Leu Thr Ser Arg Glu Val Leu Pro Gly Ala
        115                 120                 125

Lys Cys Asp Tyr Thr Ile Gln Val Gln Leu Arg Phe Cys Leu Cys Glu
130                 135                 140

Thr Ser Cys Pro Gln Glu Asp Tyr Phe Pro Pro Asn Leu Phe Val Lys
145                 150                 155                 160

Val Asn Gly Lys Leu Cys Pro Leu Pro Gly Tyr Leu Pro Pro Thr Lys
                165                 170                 175

Asn Gly Ala Glu Pro Lys Arg Pro Ser Arg Pro Ile Asn Ile Thr Pro
            180                 185                 190

Leu Ala Arg Leu Ser Ala Thr Val Pro Asn Thr Ile Val Val Asn Trp
        195                 200                 205

Ser Ser Glu Phe Gly Arg Asn Tyr Ser Leu Ser Val Tyr Leu Val Arg
210                 215                 220

Gln Leu Thr Ala Gly Thr Leu Leu Gln Lys Leu Arg Ala Lys Gly Ile
225                 230                 235                 240

Arg Asn Pro Asp His Ser Arg Ala Leu Ile Lys Glu Lys Leu Thr Ala
            245                 250                 255

Asp Pro Asp Ser Glu Val Ala Thr Thr Ser Leu Arg Val Ser Leu Met
        260                 265                 270

Cys Pro Leu Gly Lys Met Arg Leu Thr Val Pro Cys Arg Ala Leu Thr
    275                 280                 285

Cys Ala His Leu Gln Ser Phe Asp Ala Ala Leu Tyr Leu Gln Met Asn
    290                 295                 300

Glu Lys Lys Pro Thr Trp Thr Cys Pro Val Cys Asp Lys Lys Ala Pro
305                 310                 315                 320

Tyr Glu Ser Leu Ile Ile Asp Gly Leu Phe Met Glu Ile Leu Xaa Ser
            325                 330                 335

Cys Ser Asp Cys Asp Glu Ile Gln Phe Met Glu Asp Gly Ser Trp Cys
        340                 345                 350
```

-continued

```
Pro Met Lys Pro Lys Lys Glu Ala Ser Glu Val Cys Pro Pro Gly
        355                 360                 365

Tyr Gly Leu Asp Gly Leu Gln Tyr Ser Pro Val Gln Xaa Gly Xaa Pro
    370                 375                 380

Ser Glu Asn Lys Lys Xaa Val Glu Val Ile Asp Leu Thr Ile Glu Ser
385                 390                 395                 400

Ser Ser Asp Glu Glu Asp Leu Pro Pro Thr Lys Lys His Cys Xaa Val
                405                 410                 415

Thr Ser Ala Ala Ile Pro Ala Leu Pro Gly Ser Lys Gly Xaa Leu Thr
                420                 425                 430

Ser Gly His Gln Pro Ser Ser Val Leu Arg Ser Pro Ala Met Gly Thr
            435                 440                 445

Leu Gly Xaa Asp Phe Leu Ser Ser Leu Pro Leu His Glu Tyr Pro Pro
    450                 455                 460

Ala Phe Pro Leu Gly Ala Asp Ile Gln Gly Leu Asp Leu Phe Ser Phe
465                 470                 475                 480

Leu Gln Thr Glu Ser Gln His Tyr Xaa Pro Ser Val Ile Thr Ser Leu
                485                 490                 495

Asp Glu Gln Asp Xaa Leu Gly His Phe Phe Gln Xaa Arg Gly Thr Pro
                500                 505                 510

Xaa His Phe Leu Gly Pro Leu Ala Pro Thr Leu Gly Ser Ser His Xaa
    515                 520                 525

Ser Ala Thr Pro Ala Pro Xaa Pro Gly Arg Val Ser Ser Ile Val Ala
    530                 535                 540

Pro Gly Xaa Xaa Leu Arg Glu Gly His Gly Gly Pro Leu Pro Ser Gly
545                 550                 555                 560

Pro Ser Leu Thr Gly Cys Arg Ser Asp Ile Xaa Ser Leu Asp
                565                 570
```

(2) INFORMATION FOR SEQ ID NO:7:

(i) SEQUENCE CHARACTERISTICS:
        (A) LENGTH: 99 amino acids
        (B) TYPE: amino acid
        (C) STRANDEDNESS: Not Relevant
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:7:

```
Thr Trp Thr Cys Pro Val Cys Asp Lys Lys Ala Pro Tyr Glu Ser Leu
1               5                   10                  15

Ile Ile Asp Gly Leu Phe Met Glu Ile Leu Asn Ser Cys Ser Asp Cys
            20                  25                  30

Asp Glu Ile Gln Phe Met Glu Asp Gly Ser Trp Cys Pro Met Lys Pro
                35                  40                  45

Lys Lys Glu Ala Ser Glu Val Cys Pro Pro Gly Tyr Gly Leu Asp
    50                  55                  60

Gly Leu Gln Tyr Ser Pro Val Gln Glu Gly Asn Gln Ser Glu Asn Lys
65                  70                  75                  80

Lys Arg Val Glu Val Ile Asp Leu Thr Ile Glu Ser Ser Ser Asp Glu
                85                  90                  95

Glu Asp Leu
```

(2) INFORMATION FOR SEQ ID NO:8:

(i) SEQUENCE CHARACTERISTICS:
        (A) LENGTH: 167 amino acids
        (B) TYPE: amino acid
        (C) STRANDEDNESS: Not Relevant
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:8:

```
Pro Pro Thr Lys Lys His Cys Ser Val Thr Ser Ala Ala Ile Pro Ala
1               5                   10                  15

Leu Pro Gly Ser Lys Gly Val Leu Thr Ser Gly His Gln Pro Ser Ser
            20                  25                  30

Val Leu Arg Ser Pro Ala Met Gly Thr Leu Gly Gly Asp Phe Leu Ser
        35                  40                  45

Ser Leu Pro Leu His Glu Tyr Pro Pro Ala Phe Pro Leu Gly Ala Asp
    50                  55                  60

Ile Gln Gly Leu Asp Leu Phe Ser Phe Leu Gln Thr Glu Ser Gln His
65                  70                  75                  80

Tyr Gly Pro Ser Val Ile Thr Ser Leu Asp Glu Gln Asp Ala Leu Gly
                85                  90                  95

His Phe Phe Gln Tyr Arg Gly Thr Pro Ser His Phe Leu Gly Pro Leu
            100                 105                 110

Ala Pro Thr Leu Gly Ser Ser His Cys Ser Ala Thr Pro Ala Pro Pro
        115                 120                 125

Pro Gly Arg Val Ser Ser Ile Val Ala Pro Gly Gly Ala Leu Arg Glu
    130                 135                 140

Gly His Gly Gly Pro Leu Pro Ser Gly Pro Ser Leu Thr Gly Cys Arg
145                 150                 155                 160

Ser Asp Ile Ile Ser Leu Asp
                165
```

(2) INFORMATION FOR SEQ ID NO:9:

(i) SEQUENCE CHARACTERISTICS:
        (A) LENGTH: 167 amino acids
        (B) TYPE: amino acid
        (C) STRANDEDNESS: Not Relevant
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:9:

```
Pro Pro Thr Lys Lys His Cys Pro Val Thr Ser Ala Ala Ile Pro Ala
1               5                   10                  15

Leu Pro Gly Ser Lys Gly Ala Leu Thr Ser Gly His Gln Pro Ser Ser
            20                  25                  30

Val Leu Arg Ser Pro Ala Met Gly Thr Leu Gly Ser Asp Phe Leu Ser
        35                  40                  45

Ser Leu Pro Leu His Glu Tyr Pro Pro Ala Phe Pro Leu Gly Ala Asp
    50                  55                  60
```

```
Ile Gln Gly Leu Asp Leu Phe Ser Phe Leu Gln Thr Glu Ser Gln His
 65                  70                  75                  80

Tyr Ser Pro Ser Val Ile Thr Ser Leu Asp Glu Gln Asp Thr Leu Gly
                 85                  90                  95

His Phe Phe Gln Phe Arg Gly Thr Pro Pro His Phe Leu Gly Pro Leu
            100                 105                 110

Ala Pro Thr Leu Gly Ser Ser His Arg Ser Ala Thr Pro Ala Pro Ala
            115                 120                 125

Pro Gly Arg Val Ser Ser Ile Val Ala Pro Gly Ser Ser Leu Arg Glu
        130                 135                 140

Gly His Gly Gly Pro Leu Pro Ser Gly Pro Ser Leu Thr Gly Cys Arg
145                 150                 155                 160

Ser Asp Val Ile Ser Leu Asp
                165

(2) INFORMATION FOR SEQ ID NO:10:

(i) SEQUENCE CHARACTERISTICS:
        (A) LENGTH: 98 amino acids
        (B) TYPE: amino acid
        (C) STRANDEDNESS: Not Relevant
        (D) TOPOLOGY: linear (ii) MOLECULE TYPE: peptide (ix) FEATURE:
        (A) NAME/KEY: Peptide
        (B) LOCATION: 25..26
        (D) OTHER INFORMATION: /note= "serine or asparagine"

(ix) FEATURE:
        (A) NAME/KEY: Peptide
        (B) LOCATION: 61..62
        (D) OTHER INFORMATION: /note= "glycine or glutamic acid"

(ix) FEATURE:
        (A) NAME/KEY: Peptide
        (B) LOCATION: 63..64
        (D) OTHER INFORMATION: /note= "aspartic acid or
            asparagine"

(ix) FEATURE:
        (A) NAME/KEY: Peptide
        (B) LOCATION: 64..65
        (D) OTHER INFORMATION: /note= "proline or glutamine"

(ix) FEATURE:
        (A) NAME/KEY: Peptide
        (B) LOCATION: 70..71
        (D) OTHER INFORMATION: /note= "lysine or arginine"

(xi) SEQUENCE DESCRIPTION: SEQ ID NO:10:

Trp Thr Cys Pro Val Cys Asp Lys Lys Ala Pro Tyr Glu Ser Leu Ile
  1               5                  10                  15

Ile Asp Gly Leu Phe Met Glu Ile Leu Xaa Ser Cys Ser Asp Cys Asp
                 20                  25                  30

Glu Ile Gln Phe Met Glu Asp Gly Ser Trp Cys Pro Met Lys Pro Lys
             35                  40                  45

Lys Glu Ala Ser Glu Val Cys Pro Pro Gly Tyr Gly Leu Asp Gly
 50                  55                  60

Leu Gln Tyr Ser Pro Val Gln Xaa Gly Xaa Pro Ser Glu Asn Lys Lys
 65                  70                  75                  80

Xaa Val Glu Val Ile Asp Leu Thr Ile Glu Ser Ser Ser Asp Glu Glu
                 85                  90                  95

Asp Leu
```

(2) INFORMATION FOR SEQ ID NO:11:

(i) SEQUENCE CHARACTERISTICS:
        (A) LENGTH: 167 amino acids
        (B) TYPE: amino acid
        (C) STRANDEDNESS: Not Relevant
        (D) TOPOLOGY: linear (ii) MOLECULE TYPE: peptide (ix) FEATURE:
        (A) NAME/KEY: Peptide
        (B) LOCATION: 8..9
        (D) OTHER INFORMATION: /note= "serine or proline"

(ix) FEATURE:
        (A) NAME/KEY: Peptide
        (B) LOCATION: 23..24
        (D) OTHER INFORMATION: /note= "valine or alanine"

(ix) FEATURE:
        (A) NAME/KEY: Peptide
        (B) LOCATION: 44..45
        (D) OTHER INFORMATION: /note= "glycine or serine"

(ix) FEATURE:
        (A) NAME/KEY: Peptide
        (B) LOCATION: 82..83
        (D) OTHER INFORMATION: /note= "glycine or serine"

(ix) FEATURE:
        (A) NAME/KEY: Peptide
        (B) LOCATION: 94..95
        (D) OTHER INFORMATION: /note= "alanine or threonine"

(ix) FEATURE:
        (A) NAME/KEY: Peptide
        (B) LOCATION: 101..102
        (D) OTHER INFORMATION: /note= "tyrosine or phenylalanine"

(ix) FEATURE:
        (A) NAME/KEY: Peptide
        (B) LOCATION: 106..107
        (D) OTHER INFORMATION: /note= "serine or proline"

(ix) FEATURE:
        (A) NAME/KEY: Peptide
        (B) LOCATION: 121..122
        (D) OTHER INFORMATION: /note= "cystine or alanine"

(ix) FEATURE:
        (A) NAME/KEY: Peptide
        (B) LOCATION: 128..129
        (D) OTHER INFORMATION: /note= "proline or alanine"

(ix) FEATURE:
        (A) NAME/KEY: Peptide
        (B) LOCATION: 140..141
        (D) OTHER INFORMATION: /note= "glycine or serine"

(ix) FEATURE:
        (A) NAME/KEY: Peptide
        (B) LOCATION: 141..142
        (D) OTHER INFORMATION: /note= "alanine or serine"

(ix) FEATURE:
        (A) NAME/KEY: Peptide
        (B) LOCATION: 164..165
        (D) OTHER INFORMATION: /note= "isoleucine or valine"

(xi) SEQUENCE DESCRIPTION: SEQ ID NO:11:

```
Pro Pro Thr Lys Lys His Cys Xaa Val Thr Ser Ala Ala Ile Pro Ala
 1               5                  10                  15

Leu Pro Gly Ser Lys Gly Xaa Leu Thr Ser Gly His Gln Pro Ser Ser
            20                  25                  30
```

-continued

```
Val Leu Arg Ser Pro Ala Met Gly Thr Leu Gly Xaa Asp Phe Leu Ser
        35                  40                  45

Ser Leu Pro Leu His Glu Tyr Pro Pro Ala Phe Pro Leu Gly Ala Asp
        50                  55                  60

Ile Gln Gly Leu Asp Leu Phe Ser Phe Leu Gln Thr Glu Ser Gln His
65                  70                  75                  80

Tyr Xaa Pro Ser Val Ile Thr Ser Leu Asp Glu Gln Asp Xaa Leu Gly
                85                  90                  95

His Phe Phe Gln Xaa Arg Gly Thr Pro Xaa His Phe Leu Gly Pro Leu
            100                 105                 110

Ala Pro Thr Leu Gly Ser Ser His Xaa Ser Ala Thr Pro Ala Pro Xaa
            115                 120                 125

Pro Gly Arg Val Ser Ser Ile Val Ala Pro Gly Xaa Xaa Leu Arg Glu
        130                 135                 140

Gly His Gly Gly Pro Leu Pro Ser Gly Pro Ser Leu Thr Gly Cys Arg
145                 150                 155                 160

Ser Asp Ile Xaa Ser Leu Asp
                165
```

(2) INFORMATION FOR SEQ ID NO:12:

(i) SEQUENCE CHARACTERISTICS:
        (A) LENGTH: 26 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:12:

```
Ala Thr Gly Ala Ala Gly Ala Thr Cys Ala Ala Ala Gly Ala Gly Cys
1               5                   10                  15

Thr Thr Thr Ala Cys Cys Gly Ala Cys Gly
                20                  25
```

(2) INFORMATION FOR SEQ ID NO:13:

(i) SEQUENCE CHARACTERISTICS:
        (A) LENGTH: 23 amino acids
        (B) TYPE: amino acid
        (C) STRANDEDNESS: Not Relevant
        (D) TOPOLOGY: Not Relevant (v) FRAGMENT TYPE: linear (xi) SEQUENCE DESCRIPTION: SEQ ID NO:13:

```
Thr Cys Ala Gly Thr Cys Cys Ala Gly Gly Gly Ala Ala Ala Thr Cys
1               5                   10                  15

Ala Thr Gly Ala Cys Cys Gly
                20
```